(12) United States Patent
Lieberman et al.

(10) Patent No.: US 8,389,486 B2
(45) Date of Patent: Mar. 5, 2013

(54) METHODS FOR TREATING HEMATOPOIETIC MALIGNANCIES

(75) Inventors: Judy Lieberman, Brookline, MA (US); Francisco Navarro, Brookline, MA (US)

(73) Assignees: Rosetta Genomics, Ltd, Rehovot (IL); Immune Disease Institute, Boston, MA (US)

( * ) Notice: Subject to any disclaimer, the term of this patent is extended or adjusted under 35 U.S.C. 154(b) by 0 days.

(21) Appl. No.: 12/524,524

(22) PCT Filed: Jan. 25, 2008

(86) PCT No.: PCT/US2008/052086
§ 371 (c)(1),
(2), (4) Date: Jul. 24, 2009

(87) PCT Pub. No.: WO2008/092099
PCT Pub. Date: Jul. 31, 2008

(65) Prior Publication Data
US 2010/0113560 A1 May 6, 2010

Related U.S. Application Data

(60) Provisional application No. 60/886,851, filed on Jan. 26, 2007.

(51) Int. Cl.
*C12N 15/11* (2006.01)
(52) U.S. Cl. .................................................. 514/44 A
(58) Field of Classification Search ................. 514/44 A
See application file for complete search history.

(56) References Cited

U.S. PATENT DOCUMENTS

| | | | |
|---|---|---|---|
| 5,034,506 | A | 7/1991 | Summerton et al. |
| 5,235,033 | A | 8/1993 | Summerton et al. |
| 6,506,559 | B1 | 1/2003 | Fire et al. |
| 2005/0107325 | A1 | 5/2005 | Manoharan et al. |
| 2005/0182005 | A1 | 8/2005 | Tuschl et al. |
| 2005/0261218 | A1 * | 11/2005 | Esau et al. ............ 514/44 |

FOREIGN PATENT DOCUMENTS

| | | |
|---|---|---|
| WO | WO 93/23569 A1 | 11/1993 |
| WO | WO 94/02595 A1 | 2/1994 |
| WO | WO 99/04819 A1 | 2/1999 |
| WO | WO 99/05094 A1 | 2/1999 |
| WO | WO 2005047504 A1 * | 5/2005 |

OTHER PUBLICATIONS

Bartel et al. "MicroRNAs: At the Root of Plant Development?", Plant Physiology, Jun. 2003, vol. 132, pp. 709-717.
Bartel et al., "MicroRNAs: Genomics, Biogenesis, Mechanism and Function", Cell, Jan. 23, 2004, vol. 116, pp. 281-297.
Brennecke et al., "Principles of MicroRNA-Target Recognition", PLoS Biology, Mar. 205, vol. 3, Issue 3, pp. 1-15.
Doench et al., "Specificity of microRNA target selection in translational repression", Genes & Development, 2004, pp. 1-8.
Hofacker et al., "Fast Folding and Comparison of RNA Secondary Structures", Chemical Monthly, 1694, vol. 125, pp. 167-188.
Krek et al., "Combinatorial microRNA target predictions", Nature Genetics, Apr. 2005, vol. 37, pp. 1-6.
Krutzfeldt et al., "Silencing of microRNAs in vivo with 'antagomirs'", Nature, 438: pp. 1-5.
Soutschek et al., "Therapeutic silencing of an endogenous gene by systemic administration of modified siRNAs", Nature, Nov. 11, 2004, vol. 432, pp. 173-178.
Yekta et al., "MicroRNA-Directed Cleavage of HOXB8 mRNA", Science, Apr. 23, 2004, vol. 304, pp. 594-596.

* cited by examiner

Primary Examiner — Jon E Angell
(74) Attorney, Agent, or Firm — Polsinelli Shughart PC; Teddy C. Scott, Jr.; Ron Galant

(57) ABSTRACT

Described herein are compositions and methods for the prevention and treatment of hematopoietic malignancies. The compositions are miRNAs and associated nucleic acids.

10 Claims, 10 Drawing Sheets

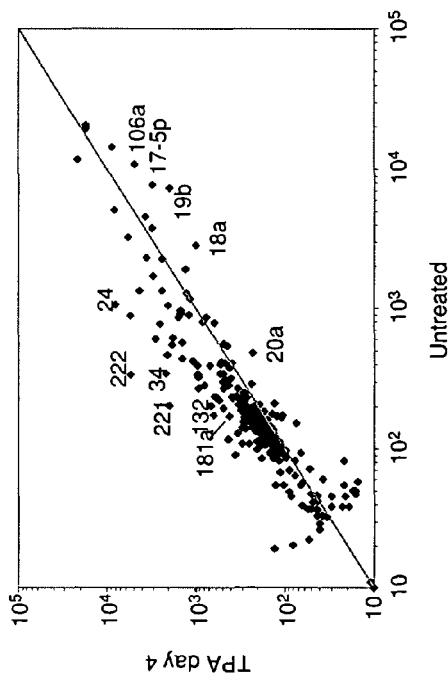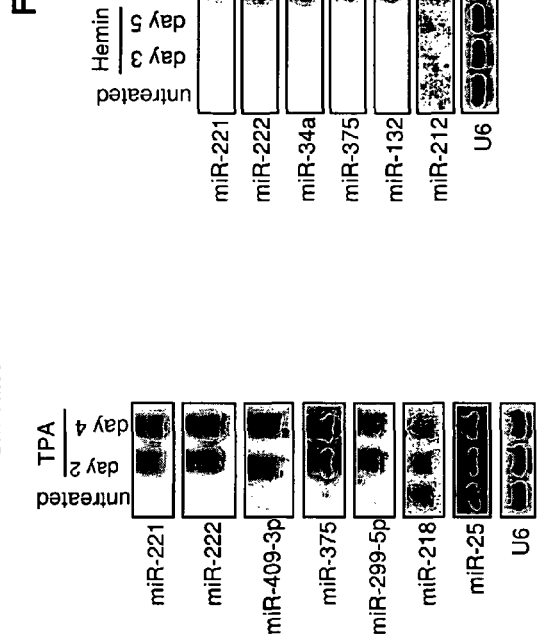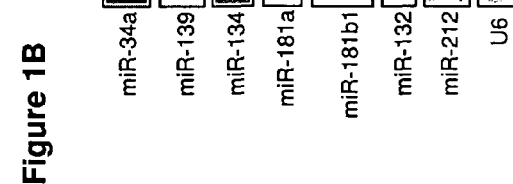
Figure 1A
Figure 1B
Figure 1C

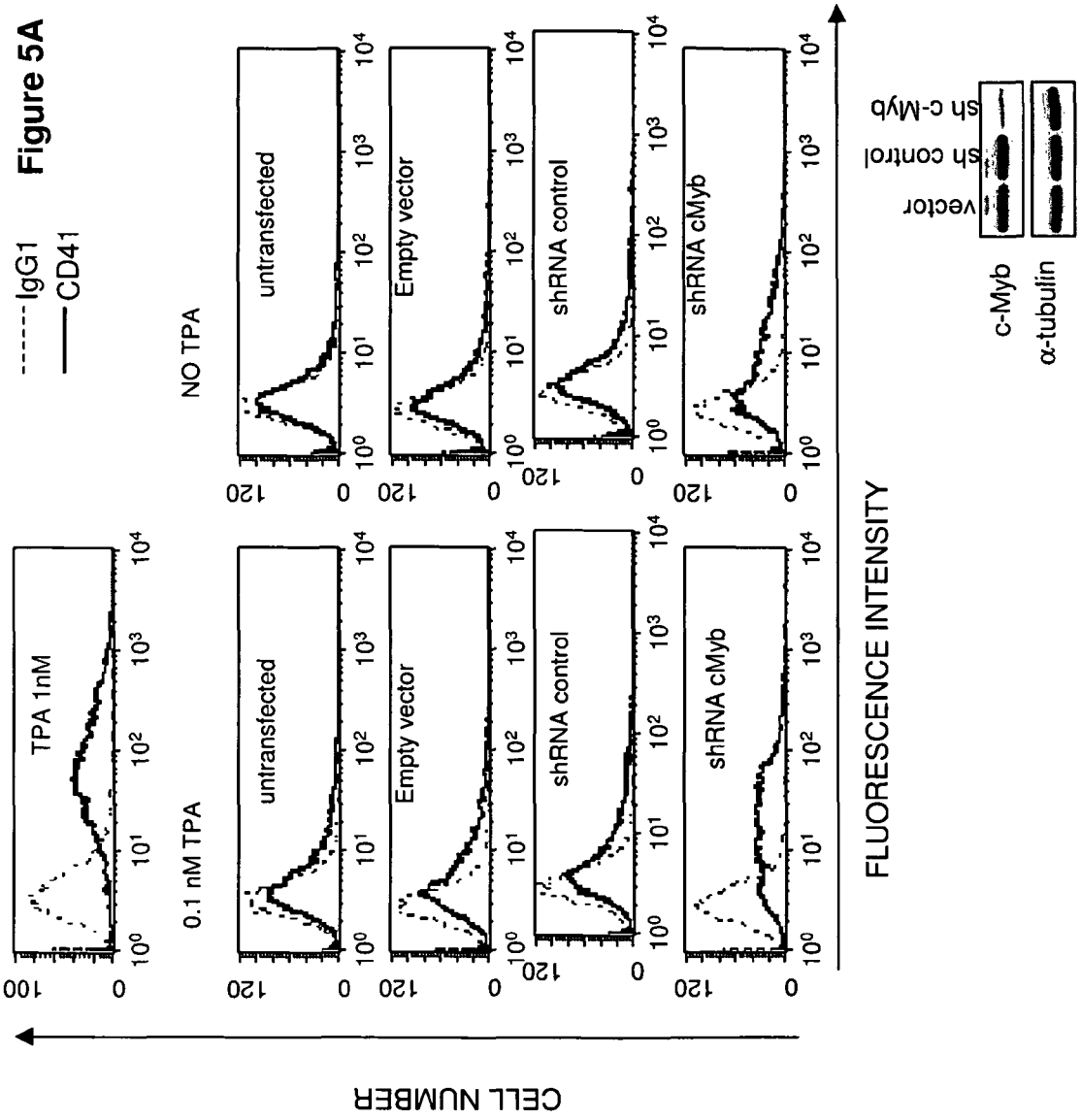

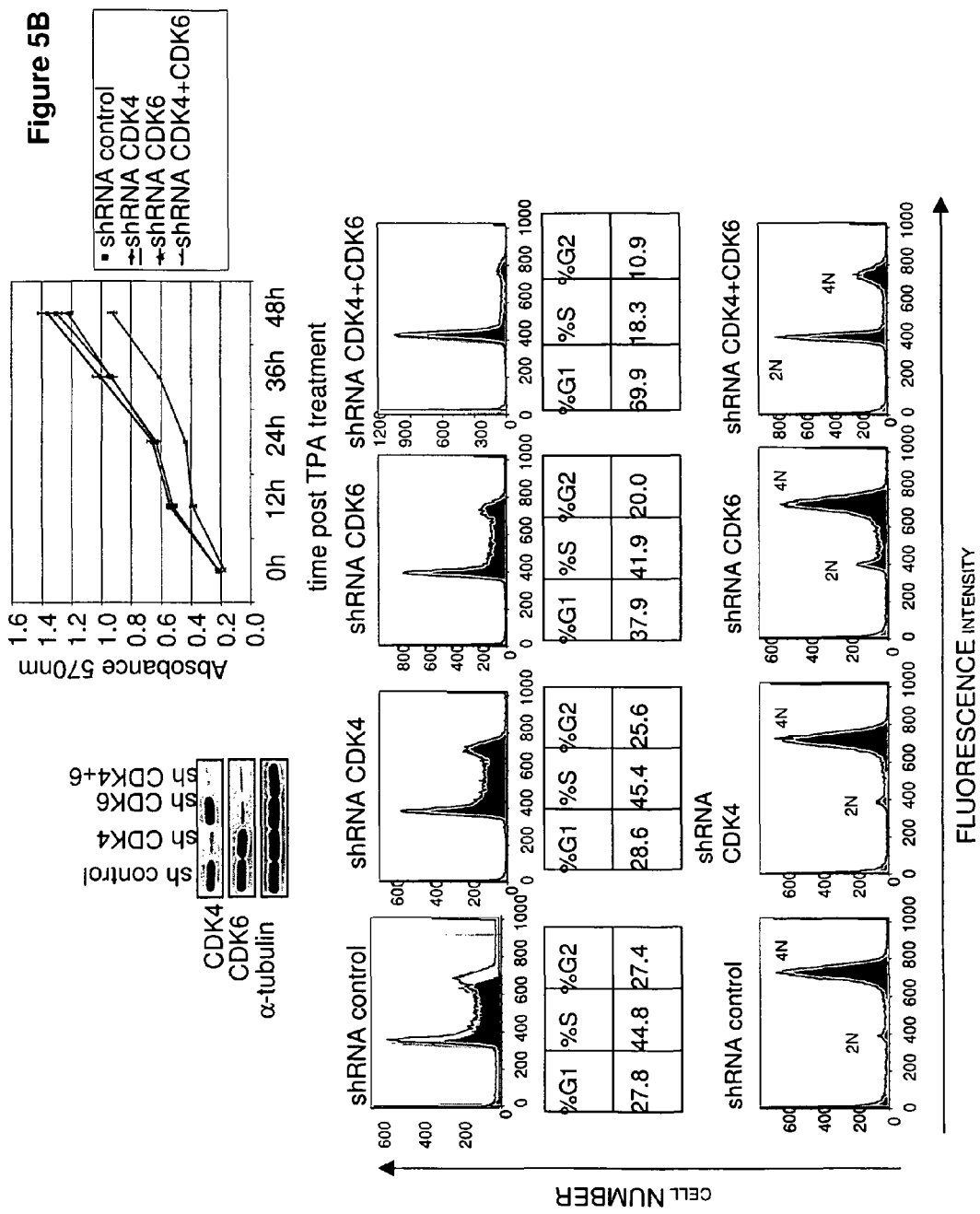

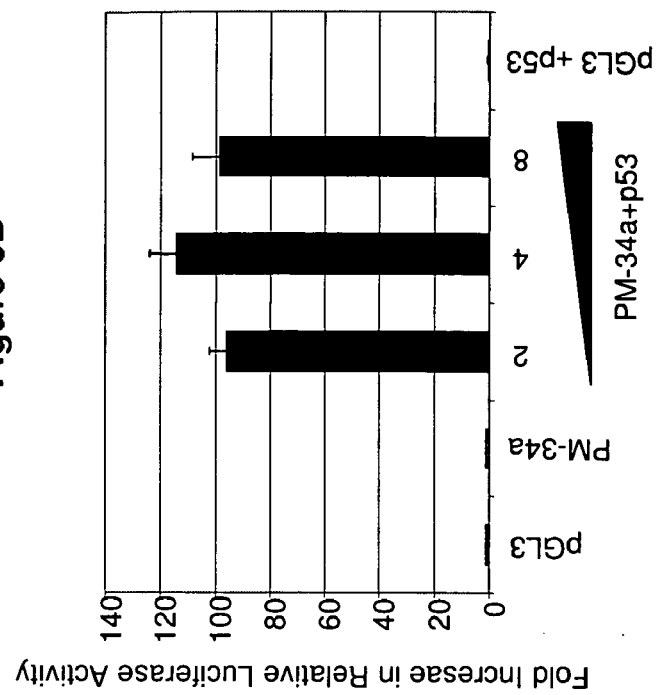
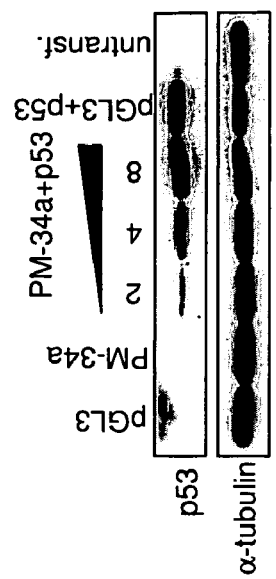
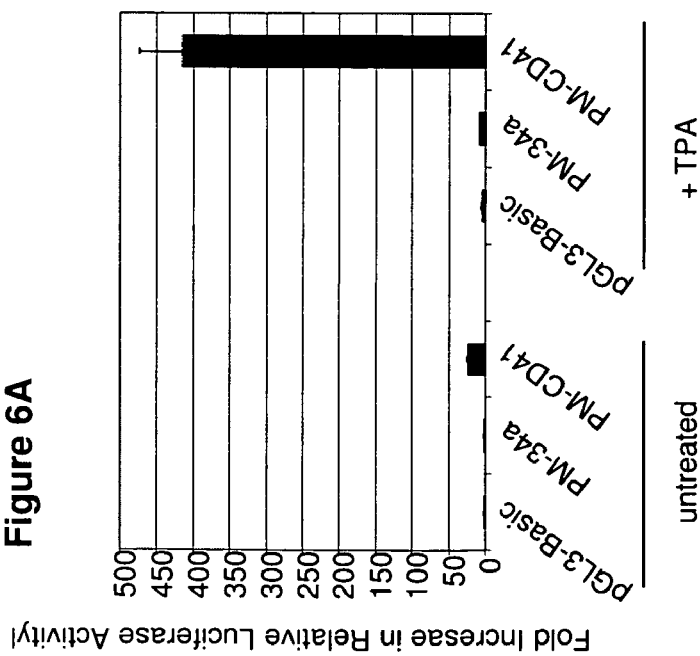
Figure 6A
Figure 6B

US 8,389,486 B2

METHODS FOR TREATING HEMATOPOIETIC MALIGNANCIES

CROSS-REFERENCE TO RELATED APPLICATIONS

This is the national stage of International Application No. PCT/US08/52086, filed on Jan. 25, 2006, which claims the benefit of U.S. Provisional Patent Application No. 60/886,851, filed on Jan. 26, 2007, the contents of both of which are incorporated herein by reference.

FIELD OF THE INVENTION

The invention relates to compositions and methods for the prevention and treatment of hematopoietic malignancies.

BACKGROUND OF THE INVENTION

The proliferation and differentiation of cells in multicellular organisms is subject to a highly regulated process. A distinguishing feature of cancer cells is the absence of control over this process; proliferation and differentiation become deregulated resulting in uncontrolled growth. MicroRNAs (miRNAs) are important regulators of gene expression and can play crucial roles during development and differentiation.

Hematopoiesis is a highly structured differentiation process in which tight control of gene expression is required for proper generation of mature blood cells. The coordinated control of gene expression is exerted at multiple levels. External signals from the microenvironment can drive the differentiation of hematopoietic stem cells (HSC) towards different lineages. In addition, the expression levels of particular transcription factors are key determinants for differentiation to several lineages.

Hematopoietic malignancies are malignant blood diseases including various lymphomas and leukemias. Leukemias result from disruption of differentiation of early blood cell precursors that proliferate uncontrollably and fail to develop into mature cells. Pharmacological agents that induce terminal differentiation of cancer cells have been used to treat some leukemias. Furthermore, these agents have allowed the development of suitable model systems to study hematopoiesis. However, the molecular mechanisms that govern differentiation of normal and leukemic blood cells are still poorly understood.

Leukemic cell lines have been routinely used as models to study hematopoietic cell differentiation in vitro. The human erythroleukemia cell line K562, which was derived from a patient with chronic myelogenous leukemia (CML), resembles a bipotent megakaryocytic-erythroid progenitor since it can undergo differentiation to both cell lineages depending on the stimulus. Phorbol esters such as 12-O-tetradecanoyl-phorbol-13-acetate (TPA) induce megakaryocytic differentiation while other agents such as hemin, sodium butirate or Ara-C induce differentiation to erythrocytes. TPA-induced megakaryocytic differentiation of leukemic K562 cells is accompanied by characteristic changes in cell morphology, cell adhesion, cell cycle arrest, endomitosis and expression of megakaryocyte lineage-specific markers such as platelet-derived growth factor and integrins $\alpha_{IIb}\beta_3$ (CD41/CD61) and $\alpha_2\beta_1$ (CD49b).

There is an unmet need for new compositions and methods for inhibiting the growth of hematopoietic malignant cells.

SUMMARY OF THE INVENTION

The present invention provides compositions and methods for treating and differentiating hematopoietic malignancies, including but not limited to, chronic myeloid leukemia, acute myeloid leukemia, acute lymphocytic leukemia, chronic lymphocytic leukemia, erythroleukemia, myeloproliferative syndromes, polycythemia vera, essential thrombocytosis, myelodysplastic syndromes, cutaneous T-Cell lymphoma, hairy cell leukemia, Hodgkin's lymphoma, non-Hodgkin's lymphoma and plasma cell neoplasms.

An isolated nucleic acid is provided. The nucleic acid may comprise a sequence of any of SEQ ID NOS: 13-32, the complementary sequence thereof, or a sequence at least 80% identical thereto. The nucleic acid may comprise a modified base.

A probe comprising the nucleic acid is also provided. A composition comprising the probe is also provided. A biochip comprising the probe is also provided.

A method for treating in vivo or ex vivo hematologic neoplasms is also provided. The method may comprise administering to a subject in need thereof or to cells harvested from said subject an effective amount of a composition comprising a nucleic acid sequence selected from the group consisting of SEQ ID NOS:1-12, or a sequence at least about 80% identical thereto.

A method for inducing suppression of lymphocyte proliferation is also provided. The method may comprise administering to a subject in need thereof or to cells harvested from said subject an effective amount of a nucleic acid sequence selected from the group consisting of SEQ ID NOS:1-12, or a sequence at least about 80% identical thereto.

A method for inducing differentiation of multipotent cells to megakaryocytes is also provided. The method may comprise administration of an amount of a composition comprising a nucleic acid sequence selected from the group consisting of SEQ ID NOS: 1-12, or a sequence at least about 80% identical thereto.

A method for modulating a first nucleic acid is also provided. The method may comprise modulating a first nucleic acid comprising the nucleotide sequence selected from the group consisting of (a) any one of SEQ ID NOS: 13-32, (b) fully complementary sequence of (a), and (c) sequence at least about 80% identical to (a) or (b). The method may further comprise introducing a second nucleic acid to the first nucleic acid wherein the second nucleic acid is selected from the group consisting of (a) SEQ ID NOS: 1-12, and (b) sequence at least about 80% identical to (a), wherein the second nucleic acid modulates expression of the first nucleic acid. The first nucleic acid may be a target sequence of c-myb, CDK4 or CDK6. The second nucleic acid may be a miRNA or siRNA.

A method of modulating the expression level of c-myb, CDK4 or CDK6 is also provided. The method may comprise introducing to a subject in need thereof an effective amount of a composition comprising a nucleic acid sequence selected from the group consisting of (a) SEQ ID NOS: 1-12, and (b) sequence at least about 80% identical to (a).

A method of modulating c-myb, CDK4 or CDK6 expression is also provided. The method may comprise introducing a first nucleic acid sequence selected from the group consisting of (a) SEQ ID NOS:1-12 and (b) sequence at least about 80% identical to (a) to a second nucleic acid sequence selected from the group consisting of (a) any one of SEQ ID NOS: 13-32, (b) fully complementary sequence of (a), and (c) sequence at least about 80% identical to (a) or (b), and wherein c-myb, CDK4 or CDK6 expression is inhibited.

A method for inducing differentiation of a hematopoietic cell is also provided. The method may comprise introducing an effective amount of a composition comprising a nucleic acid sequence selected from the group consisting of (a) SEQ ID NOS: 1-12, and (b) sequence at least about 80% identical to (a). The method may also comprise differentiation of a hematopoietic cell wherein the hematopoietic cell is selected from the group consisting of lymphoid progenitor cell, a myeloid progenitor cell, a natural kill cell, a T cell, a B cell, a plasma cell, a erythrocytes, a megakaryocytes, monocytes, macrophages, and granulocytes. The method may also comprise differentiation of a hematopoietic cell wherein the granulocyte cell is selected from the group consisting of neutrophils, basophils, and eosinophis.

A method for treating a hematologic neoplasm is also provided. The method may comprise administering to a subject in need thereof an effective amount of a composition comprising a nucleic acid sequence selected from the group consisting of (a) SEQ ID NOS: 1-12, and (b) sequence at least about 80% identical to (a). The method may also comprise treating ex vivo and in vivo. The hematologic neoplasm may be relapsed Hodgkin's disease, resistant Hodgkin's disease high grade, low grade and intermediate grade non-Hodgkin's lymphomas, B cell chronic lymphocytic leukemia (B-CLL), lymphoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, angioimmunoblastic lymphoadenopathy, small lymphocytic, follicular, diffuse large cell, diffuse small cleaved cell, large cell immunoblastic lymphoblastoma, small, non-cleaved, Burkitt's and non-Burkitt's, follicular, predominantly large cell; follicular, predominantly small cleaved cell; and follicular, mixed small cleaved and large cell lymphomas.

A method for modulating a first nucleic acid that is involved in hematopoietic cell differentiation is also provided. The method may comprise introducing a second nucleic acid to the first nucleic acid. The second nucleic acid may modulate the expression of the first nucleic acid. The second nucleic acid may also be capable of increasing hematopoietic stem cell differentiation. The second nucleic acid may be selected from the group consisting of a (a) miRNA, (b) synthetic or mimic miRNA, (c) interfering RNA such as a siRNA, (d) polycistronic nucleic acid comprising one or more miRNAs, or (e) plurality of the nucleic acids of (a)-(d).

A method for identifying a nucleic acid that differentiates a leukemia or myeloproliferative cell is also provided. The method may comprise introducing a nucleic acid into a leukemia or myeloproliferative cell. The method may also comprise measuring the differentiation state of the cell. The differentiation state of the cell compared to a control may be indicative of a nucleic acid capable of differentiating a leukemia or myeloproliferative cell. The nucleic acid may be a (a) miRNA, (b) synthetic or mimic miRNA, (c) interfering RNA such as a siRNA, (d) polycistronic nucleic acid comprising one or more miRNAs, or (e) a plurality of the nucleic acids of (a)-(d). Measuring the differentiation state of the cell may be by a molecular marker. The molecular marker may be indicative of a differentiated leukemia or myeloproliferative cell. The molecular marker may be CD41, CD41a, CD61 or CD42b. The leukemia or myeloproliferative cell may be frozen in an undifferentiated state.

These and other embodiments of the present invention will become apparent in conjunction with the figures, description and claims that follow.

BRIEF DESCRIPTION OF THE DRAWINGS

FIG. 1 demonstrates miRNA signature of TPA-induced megakaryocyte differentiated K562 cells. (A). miRNA expression profile during megakaryocytic differentiation of K562 cells using miR-Chip microarrays. The diagram represents the values corresponding to the raw signal intensity obtained for each miRNA in untreated vs. TPA-treated (100 ng/ml) K562 cells for 4 days. Depicted are selected miRNAs with significant differential expression in TPA-differentiated cells compared to untreated cells. (B). Validation of the miR-Chip microarray results using northern blot. 40 ng of total RNA from untreated or TPA-treated K562 cells for 2 or 4 days were resolved in 15% TBE-Urea acrylamide gels. RNA was transfer to Nylon Membranes and UV-crosslinked. The membranes were prehybridyzed and then hybridized with a α32P dATP 3' end labeled oligoprobe against the miRNA of interest. After washing, the membranes were developed using a PhosphorImager. As loading control the membranes were also probed with an oligonucleotide against snRNA U6. (C). Analysis of lineage specificity of TPA upregulated miRNAs. Northern blot analysis, as described above, of K562 cells treated with hemin (100 µM) for 3 or 5 days. The percentage of hemoglobin producing cells at day 3 and day 5 was 63 and 68% respectively, as determined by benzidine staining (not shown). As positive control 40 µg of RNA from K562 cells treated with TPA for 4 days were run in parallel.

FIG. 5 demonstrates functional relevance of miR-34a targets in MK differentiation of K562 cells. (A). c-myb knockdown in K562 cells induces upregulation of the MK specific marker CD41. K562 cells were transfected with a shRNA against c-myb, a hairpin control, empty vector or not transfected. 48 hours post transfection replicate samples were treated with a suboptimal amount of TPA (0.1 nM) or left untreated. CD41 expression was measured by flow cytometry 48 hours post TPA treatment. As positive control for CD41 expression K562 cells were treated with 1 nM of TPA. The bottom panel shows the level of expression of c-myb at 48 hours post-transfection and before treatment with TPA in the samples shown above. c-myb protein levels were analyzed by Western Blot and the membrane was stripped and reprobed with an MAb against α-tubulin for loading control. (B). Simultaneous knockdown of cyclin dependent kinases CDK4 and CDK6 is required for inhibition of proliferation and cell cycle arrest in K562 cells. K562 cells were transfected with the indicated shRNA and replicate samples were analyzed for cell proliferation and cell cycle profile. Immunoblot analysis of CDK4 and CDK6 knockdown in the transfected samples is shown (top left panel). Cell proliferation was evaluated using the MTT Cell Proliferation assay as described above starting the analysis 12 hours post transfection (sample designated as time 0h). Cell cycle analysis was performed 72 hours after transfection as described above (bottom panel).

FIG. 6 shows that miR-34a upregulation during TPA-induced MK differentiation of K562 cells is p53 independent. (A). The putative miR-34a promoter is not responsive to TPA stimulus. K562 cells were transfected with a firefly luciferase reporter vectors in which the luciferase activity was driven by the miR-34a promoter (PM34a) or the CD41 promoter (PM41). As negative control, cells were transfected with a promoterless luciferase vector (pGL3-Basic). Samples were also transfected with a *renilla* luciferase reporter vector for control of efficiency of transfection. 48 hours post transfection replicate samples were treated with 10 nM TPA or left untreated. The luciferase activity of the samples was measured 48 hours after TPA treatment. The firefly luciferase activity was normalized to the *renilla* luciferase activity and represented as fold increase relative to the control sample (sample transfected with the promoterless construct and not treated with TPA). (B). Exogenous expression of p53 in K562 cells is able to activate the miR-34a promoter. K562 cells were transfected with a promoterless firefly luciferase reporter vector or a reporter containing the miR-34a promoter (PM34a), a *renilla* luciferase reporter vector and increasing amounts (2, 4 and 8 µg) of pCMV-p53 vector. The total amount of transfected DNA was kept constant using an empty pCMV plasmid. The luciferase activity was measured 48 hours post transfection and was normalized as described above. The diagram represents the fold increase in luciferase activity relative to the control sample (sample transfected with the promoterless vector). The bottom panel shows the level of expression of p53 in the samples analyzed above. p53 protein levels were analyzed by Western Blot and the membrane was stripped and reprobed with an MAb against α-tubulin for loading control.

DETAILED DESCRIPTION

Figure 2B:
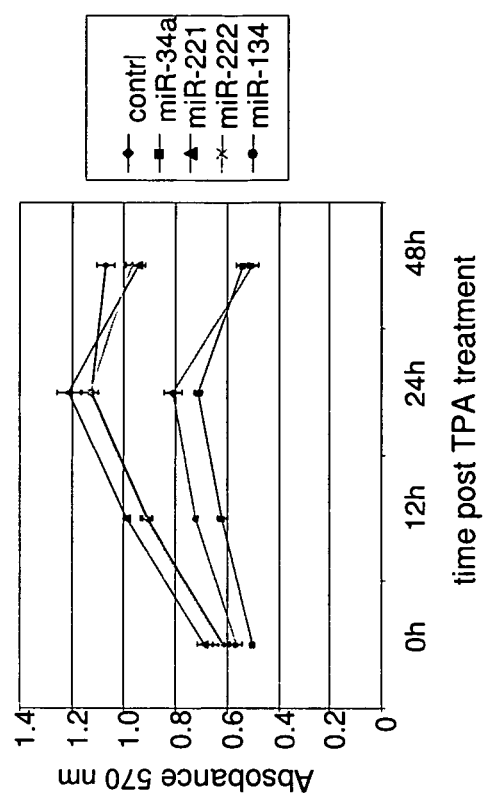
FIG. 2 shows that miRNAs 34a (SEQ ID NO: 2), 181a (SEQ ID NO: 1) and 134 (SEQ ID NO: 7) enhance megakaryocytic differentiation in K562 cells. (A). Overexpression of miR-34a or miR-181a in K562 cells induces the expression of the MK specific marker CD41. K562 cells were transfected with 3 ng of the indicated miRNA mimic and 24 hours after transfection the cells were stimulated with a sub-optimal amount of TPA (0.1 nM). CD41 expression was analyzed by FACS 72 hours post-TPA stimulation. As positive control for CD41 expression K562 cells were treated with 1 nM of TPA. (B). miRNAs 34a and 134 inhibit cell proliferation of K562 cells. The cells were transfected with the indicated miRNA and then treated with a suboptimal amount of TPA as described above. Cell proliferation rates were measured at different time points using the MTT Cell Proliferation Assay. Data is presented as raw OD570 values of triplicate samples. Error bars denote standard deviation.

The invention is based in part on the discovery that specific microRNAs (SEQ ID NOS: 1-12) may regulate differentiation of a multipotent hematopoietic cell line into megakaryocytes (MK). These microRNAs may play an important role in defining MK differentiation by downregulating the transcription factor c-myb and the cell cycle regulators CDK4 and CDK6. The majority of the predicted binding sites of the microRNAs on the 3'UTR of c-Myb, CDK4 and CDK6 (SEQ ID NOS: 13-32) were confirmed in vitro.

Understanding the role of miRNAs in regulating hematopoietic cell differentiation will open the door to exploring the possibility of developing RNAi-based drugs to mimic tumor suppressor miRNAs or antagonize the action of oncogenic miRNAs to treat leukemia and lymphoma.

Methods and compositions are provided for the prevention and treatment of hematopoietic malignancies. Other aspects of the invention will become apparent to the skilled artisan by the following description of the invention.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

1. Definitions

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

a. Aberrant Proliferation

As used herein, the term "aberrant proliferation" means cell proliferation that deviates from the normal, proper, or expected course. For example, aberrant cell proliferation may include inappropriate proliferation of cells whose DNA or other cellular components have become damaged or defective. Aberrant cell proliferation may include cell proliferation whose characteristics are associated with an indication caused by, mediated by, or resulting in inappropriately high levels of cell division, inappropriately low levels of apoptosis, or both. Such indications may be characterized, for example, by single or multiple local abnormal proliferations of cells, groups of cells, or tissue(s), whether cancerous or non-cancerous, benign or malignant.

b. Administering

As used herein, the term "administering" may mean providing a pharmaceutical agent or composition to a subject, and may include administering by a medical professional and self-administering. Administering may be performed parenterally, subcutaneously, intravenously, or intratumorally, or by chemoembolization. "Parenteral administration" may be through injection or infusion. Parenteral administration may include subcutaneous administration, intravenous administration, or intramuscular administration. "Subcutaneous administration" may be just below the skin. "Intravenous administration" may be into a vein. "Intratumoral administration" may be within a tumor. "Chemoembolization" may mean a procedure in which the blood supply to a tumor may be blocked surgically or mechanically and chemotherapeutic agents may be administered directly into the tumor.

c. Attached

"Attached" or "immobilized" as used herein to refer to a probe and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

d. Complement

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

e. Dose

"Dose" as used herein may mean a specified quantity of a pharmaceutical agent provided in a single administration. A dose may be administered in two or more boluses, tablets, or injections. For example, where subcutaneous administration is desired, the desired dose may require a volume not easily accommodated by a single injection. Two or more injections may be used to achieve the desired dose. A dose may also be administered in two or more injections to minimize injection site reaction in an individual.

f. Dosage Unit

"Dosage unit" as used herein may mean a form in which a pharmaceutical agent is provided. A dosage unit may be a vial containing lyophilized oligonucleotide or a vial containing reconstituted oligonucleotide.

g. Gene

"Gene" used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

h. Hematopoietic Cells

As used herein, the term "hematopoietic cells" may refer to blood cells including but not limited to lymphoid progenitor cells, myeloid progenitor cells, natural killer cells, T cells, B cells, plasma cells, erythrocytes, megakaryocytes, monocytes, macrophages, and granulocytes such as neutrophils, eosinophils, and basophils.

i. Host Cell

"Host cell" used herein may be a naturally occurring cell or a transformed cell that may contain a vector and may support replication of the vector. Host cells may be cultured cells, explants, cells in vivo, and the like. Host cells may be prokaryotic cells such as *E. coli*, or eukaryotic cells such as yeast, insect, amphibian, or mammalian cells, such as CHO and HeLa.

j. Identity

"Identical" or "identity" as used herein in the context of two or more nucleic acids or polypeptide sequences may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

k. Label

"Label" as used herein may mean a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

l. Leukemia

As used herein, the term "leukemia" may refer to cancers that are characterized by an uncontrolled increase in the number of at least one leukocyte and/or leukocyte precursor in the blood and/or bone marrow. Leukemias may include acute lymphoblastic leukemia (ALL); acute myeloid leukemia (AML); chronic lymphocytic leukemia (CLL); chronic myelogenous leukemia (CML); and, hairy cell leukemia. "Leukemic cells" may comprise cells of the aforementioned leukemias. The leukemia may also be erythorleukema.

m. Modified Nucleotide

"Modified nucleotide" or "modified base" as used herein may mean a nucleotide analog having one or more modifications relative to a naturally nucleotide.

A modified nucleoside may be a stabilizing nucleoside such as a sugar-modified nucleoside. The sugar-modified nucleosides may further comprise a natural or modified heterocyclic base moiety and/or a natural or modified internucleoside linkage and may include further modifications independent from the sugar modification. The sugar modified nucleoside may be a 2'-modified nucleoside, wherein the sugar ring is modified at the 2' carbon from natural ribose or 2'-deoxy-ribose. A 2'-O-methyl group may be present in the sugar residue.

A modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005), Soutschek et al., Nature 432:173-178 (2004), and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

n. Modified Oligonucleotide

"Modified oligonucleotide" as used herein may mean an oligonucleotide having one or more modifications relative to a naturally occurring terminus, sugar, nucleobase, nucleotide, and/or internucleoside linkage. A modified oligonucleotide may comprise a modified nucleotide.

A modified oligonucleotide may be a nucleobase sequence fully identical or complementary to a miRNA nucleobase sequence listed herein, or a precursor thereof. The modified oligonucleotide may have a nucleobase sequence having one mismatch with respect to the nucleobase sequence of the mature miRNA, or a precursor thereof. The modified oligonucleotide may also have a nucleobase sequence having two mismatches with respect to the nucleobase sequence of the miRNA, or a precursor thereof. The modified oligonucleotide may also have a nucleobase sequence having no more than two mismatches with respect to the nucleobase sequence of the mature miRNA, or a precursor thereof. The mismatched nucleobases may be contiguous, or they may not be contiguous.

The modified oligonucleotide may consist of a number of linked nucleosides that is equal to the length of the mature miRNA. The number of linked nucleosides of the modified oligonucleotide may be less than the length of the mature miRNA. The number of linked nucleosides of the modified oligonucleotide may be one less than the length of the mature miRNA. The modified oligonucleotide may have one less nucleoside at the 5' terminus. The modified oligonucleotide may also have one less nucleoside at the 3' terminus. The modified oligonucleotide may also have two fewer nucleosides at the 5' terminus or two fewer nucleosides at the 3' terminus. The modified oligonucleotide may have a number of linked nucleosides that is less than the length of the miRNA, wherein each nucleobase of a modified oligonucleotide is complementary to each nucleobase at a corresponding position in a miRNA, and the modified oligonucleotide may be considered to be a modified oligonucleotide having a nucleobase sequence that is fully complementary to a portion of a miRNA sequence.

The modified oligonucleotide may consists of 15 to 30 linked nucleosides. The modified oligonucleotide may also consist of 19 to 24 linked nucleosides. The modified oligonucleotide may also consist of 21 to 24 linked nucleosides. The modified oligonucleotide may consist of 15, 16, 17, 18, 19, 20, 21, 22, 23, 24, 25, 26, 27, 28, 29, or 30 linked nucleosides.

A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases. The modified oligonucleotide may comprise one or more modified nucleosides.

o. Nucleic Acid

"Nucleic acid" or "oligonucleotide" or "polynucleotide" used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. A nucleic acid may comprise a modified nucleotide or oligonucleotide, which may contain one or more non-naturally occurring or modified nucleotides.

p. Operably Linked

"Operably linked" used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

q. Probe

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

r. Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

s. Selectable Marker

"Selectable marker" used herein may mean any gene which confers a phenotype on a host cell in which it is expressed to facilitate the identification and/or selection of cells which are transfected or transformed with a genetic construct. Representative examples of selectable markers include the ampicillin-resistance gene ($Amp^r$), tetracycline-resistance gene ($Tc^r$), bacterial kanamycin-resistance gene ($Kan^r$), zeocin resistance gene, the AURI-C gene which confers resistance to the antibiotic aureobasidin A, phosphinothricin-resistance gene, neomycin phosphotransferase gene (nptII), hygromycin-resistance gene, beta-glucuronidase (GUS) gene, chloramphenicol acetyltransferase (CAT) gene, green fluorescent protein (GFP)-encoding gene and luciferase gene.

t. Stringent Hybridization Conditions

"Stringent hybridization conditions" used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

u. Substantially Complementary

"Substantially complementary" used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

v. Substantially Identical

"Substantially identical" used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

w. Subject

As used herein, the term "subject" refers to a mammal, including both human and other mammals. The methods of the present invention are preferably applied to human subjects.

x. Target

"Target" as used herein may mean a polynucleotide that may be bound by one or more probes under stringent hybridization conditions.

y. Therapeutically Effective Amount

As used herein the term "therapeutically effective amount" or "therapeutically efficient" as to a drug dosage, refer to dosage that provides the specific pharmacological response for which the drug is administered in a significant number of subjects in need of such treatment. The "therapeutically effective amount" may vary according, for example, the physical condition of the patient, the age of the patient and the severity of the disease.

z. Variant

"Variant" used herein to refer to a nucleic acid may mean (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

aa. Vector

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

2. MicroRNA

A gene coding for a miRNA may be transcribed leading to production of a miRNA precursor known as the pri-miRNA. The pri-miRNA may be part of a polycistronic RNA comprising multiple pri-miRNAs. The pri-miRNA may form a hairpin with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 30-200 nt precursor known as the pre-miRNA. Drosha may cleave the pri-miRNA with a staggered cut typical of RNase III endonucleases yielding a pre-miRNA stem loop with a 5' phosphate and ~2 nucleotide 3'overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. mRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA: miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-8 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et al 2005 Cell 120-15). Similarly, nucleotides 1-7 or 2-8 were used to identify and validate targets by Krek et al (2005, Nat Genet. 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

mRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

3. Nucleic Acid

Nucleic acids are provided herein. The nucleic acid may comprise the sequence of SEQ ID NOS: 1-32 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

a. Nucleic Acid Complexes

The nucleic acid may further comprise one or more of the following: a peptide, a protein, a RNA-DNA hybrid, an antibody, an antibody fragment, a Fab fragment, and an aptamer. The nucleic acid may also comprise a protamine-antibody fusion protein as described in Song et al (Nature Biotechnology 2005; 23:709-17) and Rossi (Nature Biotechnology 2005:23; 682-4), the contents of which are incorporated herein by reference. The protamine-fusion protein may comprise the abundant and highly basic cellular protein protamine The protamine may readily interact with the nucleic acid. The protamine may comprise the entire 51 amino acid protamine peptide or a fragment thereof. The protamine may be covalently attached to another protein, which may be a Fab. The Fab may bind to a receptor expressed on a cell surface.

b. Pri-miRNA

The nucleic acid may comprise a sequence of a pri-miRNA or a variant thereof. The pri-miRNA sequence may comprise from 45-30,000, 50-25,000,100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise the sequence of SEQ ID NOS: 1-22 or variants thereof.

The pri-miRNA may form a hairpin structure. The hairpin may comprise first and second nucleic acid sequences that are substantially complimentary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

c. Pre-miRNA

The nucleic acid may also comprise a sequence of a pre-miRNA or a variant thereof. The pre-miRNA sequence may comprise from 45-200, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-32 or variants thereof.

d. MiRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1-12 or variants thereof.

e. Anti-miRNA

The nucleic acid may also comprise a sequence of an anti-miRNA that is capable of blocking the activity of a miRNA or miRNA*, such as by binding to the pri-miRNA, pre-miRNA, miRNA or miRNA* (e.g. antisense or RNA silencing), or by binding to the target binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially identical or complimentary to the 5' of a miRNA and at least 5-12 nucleotides that are substantially complimentary to the flanking regions of the target site from the 5' end of the miRNA, or (b) at least 5-12 nucleotides that are substantially identical or complimentary to the 3' of a miRNA and at least 5 nucleotide that are substantially complimentary to the flanking region of the target site from the 3' end of the miRNA. The sequence of the anti-miRNA may comprise the compliment of SEQ ID NOS: 1-32 or variants thereof.

f. Binding Site of Target

The nucleic acid may also comprise a sequence of a target miRNA binding site, or a variant thereof. The target site sequence may comprise a total of 5-100 or 10-60 nucleotides. The target site sequence may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 or 63 nucleotides. The target site sequence may comprise at least 5 nucleotides of the sequence of SEQ ID NOS: 1-32.

4. Synthetic Gene

A synthetic gene is also provided comprising a nucleic acid described herein operably linked to a transcriptional and/or translational regulatory sequence. The synthetic gene may be capable of modifying the expression of a target gene with a binding site for a nucleic acid described herein. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

5. Vector

A vector is also provided comprising a synthetic gene described herein. The vector may be an expression vector. An expression vector may comprise additional elements. For example, the expression vector may have two replication systems allowing it to be maintained in two organisms, e.g., in one host cell for expression and in a second host cell (e.g., bacteria) for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells.

6. Host Cell

A host cell is also provided comprising a vector, synthetic gene or nucleic acid described herein. The cell may be a bacterial, fungal, plant, insect or animal cell. For example, the host cell line may be DG44 and DUXB11 (Chinese Hamster Ovary lines, DHFR minus), HELA (human cervical carcinoma), CV1 (monkey kidney line), COS (a derivative of CV1 with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). Host cell lines may be available from commercial services, the American Tissue Culture Collection or from published literature.

7. Probes

A probe is also provided comprising a nucleic acid described herein. Probes may be used for screening and diagnostic methods, as outlined below. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

8. Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

9. Compositions

A pharmaceutical composition is also provided. The composition may comprise a nucleic acid described herein and optionally a pharmaceutically acceptable carrier. The compositions may be used for therapeutic applications. The pharmaceutical composition may be administered by known methods, including wherein a nucleic acid is introduced into a desired target cell in vitro or in vivo.

The composition may encompass modified oligonucleotides that may be identical, substantially identical, substantially complementary or complementary to any nucleobase sequence version of the miRNAs described herein or a precursor thereof.

The compositions may be combined with a chemotherapeutic agent, a combination of chemotherapeutic agents and/or a radiotherapy. The chemotherapeutic agents may be 5-fluorouracil, doxorubicine, mitomycin c, etoposide, carboplatin, or cyclophosphamide.

The compositions of the present invention may be formulated into pharmaceutical compositions by combination with appropriate, pharmaceutically acceptable carriers or diluents, and can be formulated into preparations in solid, semi-solid, liquid or gaseous forms, such as tablets, capsules, powders, granules, ointments, solutions, suppositories, injections, inhalants and aerosols. As such, administration of the agents may be achieved in various ways, including oral, buccal, rectal, parenteral, intraperitoneal, intradermal, transdermal, intracheal, etc.

10. Cell Delivery

A method for delivering the nucleic acid into cells is also provided. Methods for the delivery of nucleic acid molecules are also described in Akhtar et al., (Trends Cell Bio. 2, 139, 1992), the contents of which are incorporated herein by reference. WO 94/02595 describes general methods for delivery of RNA molecules, the contents of which are incorporated by reference. These protocols may be utilized for the delivery of virtually any nucleic acid molecule. Nucleic acid molecules may be administered to cells by a variety of methods known to those familiar to the art, for example, encapsulation in liposomes, by iontophoresis, or by incorporation into other vehicles, such as hydrogels, cyclodextrins, biodegradable nanocapsules, and bioadhesive microspheres. The nucleic acid may also be endocytosed in clathrin coated pits. The vesicles may be uncoated and the nucleic acid released from the endosome to the RISC.

Alternatively, the nucleic acid/vehicle combination may be locally delivered by direct injection or by use of an infusion pump. Other routes of delivery may be oral (tablet or pill form) and/or intrathecal delivery (Gold, 1997, Neuroscience, 76, 1153-1158). Other approaches include the use of various transport and carrier systems, for example, through the use of conjugates and biodegradable polymers. More detailed descriptions of nucleic acid delivery and administration are provided for example in WO93/23569, WO99/05094, and WO99/04819, and which are incorporated herein by reference.

The nucleic acid may be delivered in vivo by the method described in Song et al (Nature Biotechnology 2005; 23:709-17) and Rossi (Nature Biotechnology 2005:23; 682-4), the contents of which are incorporated herein by reference. The method may comprise binding the nucleic acid to a receptor expressed on a cell surface. The delivery may be intratumorally or intravenously. The nucleic acids may be introduced into tissues or host cells by any number of routes, including viral infection, microinjection, or fusion of vesicles. Jet injection may also be used for intra-muscular administration, as described by Furth et al. (Anal Biochem 115 205:365-368, 1992). The nucleic acids may be coated onto gold microparticles, and delivered intradermally by a particle bombardment device, or "gene gun" as described in the literature (see, for example, Tang et al. Nature 356:152-154, 1992), where gold microprojectiles are coated with the DNA, then bombarded into skin cells.

The nucleic acids of the invention may be introduced into primary hematopoietic cells by using cell-type specific delivery of said nucleic acids complexed with antibody fragment protamine fusion proteins (as described in Song et al., Nat. Biothecnol. 23(6):709-17, 2005). The cell delivery method may allow for systemic, cell-type specific, antibody-mediated delivery of the nucleic acid. The delivery methods for nucleic acids describe above may also used to delivery compositions as described above.

11. Therapeutic

A method for treating in vivo or ex vivo hematologic neoplasms is also provided. The method may comprise administering to a subject in need thereof or to harvest the cells of said subject an effective amount of a composition comprising a nucleic acid inhibitor of a hematologic neoplasm. As previously discussed the methods, compositions and articles of manufacture of the present invention are particularly useful in the treatment of hematologic neoplasms such as chronic lymphocytic leukemia. Other CD23+ hematologic malignancies may also be treated using the disclosed methods. The hematologic malignancies may also include small T cell lymphomas, lymphocytic lymphoma, mantle cell lymphoma, Hodgkins and non-Hodgkins lymphoma as well as leukemias, including ALL-L3 (Burkitt's type leukemia), acute T cell leukemia, chronic myelogenous leukemia and monocytic cell leukemias. The method may also treat a myeloproliferative disease such as polycythemia vera or essential thrombocytosis.

The compositions and methods of the present invention in combination with chemotherapeutic agents and/or radiotherapy may also be useful in treating a variety of B-cell lymphomas, including low grade/NHL follicular cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, Waldenstrom's Macroglobulinemia, lymhoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, angioimmunoblastic lymphoadenopathy, small lymphocytic, follicular, diffuse large cell, diffuse small cleaved cell, large cell immunoblastic lymphoblastoma, small, non-cleaved, Burkitt's and non-Burkitt's, follicular, predominantly large cell; follicular, predominantly small cleaved cell; and follicular, mixed small cleaved and large cell lymphomas. See, Gaidono et al., "Lymphomas" IN CANCER: PRINCIPLES & PRACTICE OF ONCOLOGY, Vol. 2: 2131-2145 (DeVita et al., eds., $5^{th}$ ed. 1997). It should be clear to those of skill in the art that these lymphomas will often have different names due to changing systems of classification, and that patients having lymphomas classified under different names may also benefit from the combined therapeutic regimens of the present invention. In addition to the aforementioned neoplastic disorders, it will be appreciated that the disclosed invention may advantageously be used to treat additional malignancies expressing the CD23 antigen.

a. MK Differentiation

The therapeutic method described above may also include the nucleic acid being strongly upregulated in phorbol ester-differentiated K562 cells. The method may also include expression of the nucleic acid that is part of a nucleic acid expression signature that is specific to the megakaryocytic lineage. The nucleic acid may not be upregulated during hemin-induced erythroid differentiation. The nucleic acid may contribute to the process of MK differentiation in K562 cells, and may be an important regulator of megakaryocytic differentiation. Furthermore, the nucleic acids may be existing miRNA molecules that may be used as starting materials for the manufacture of sequence-modified miRNA molecules. These miRNA molecules may be modified, in order that they are processed and then generated as double-stranded siRNAs which are again directed against therapeutically relevant targets. These miRNA molecules may then be used for inducing differentiation of multipotent cells into megakaryocytes.

The method may further include enforced expression of the nucleic acid in multipotent cells to enhance MK differentiation as measured by increased expression of the MK specific marker CD41, and may also decrease cell proliferation and induces cell cycle arrest in G1. The function of the nucleic acid in megakaryopoiesis may be mediated by direct regulation of the key transcriptional hematopoietic regulator c-myb and the cell cycle regulators CDK4 and CDK6. Induction of the nucleic acid may be p53-independent. The nucleic acid may be upregulated during thrombopoietin (TPO)-induced ex vivo differentiation of CD34+ hematopoietic precursors.

b. Regulation of Transcription Factor c-myb and Expression of CDK4 and CDK6

The method may also include the nucleic acid directly regulating the levels of expression of the transcription factor c-myb because the nucleic acid may also be upregulated during differentiation of CD34+ HSC to megakaryocytes, and its expression levels may also be inversely correlated to the expression of c-myb, CDK4 and CDK6. Accordingly, the method may also use the nucleic acid to directly control the expression of the key cell cycle regulators CDK4 and CDK6. The nucleic acid may also be transcriptionally activated by the tumor suppressor p53, and may regulate the expression of numerous genes that have been previously known to be regulated by p53. Accordingly, the method may also include using the nucleic acid as an important regulator of cell proliferation in leukemic cells.

Having now generally described the invention, the same will be more readily understood through reference to the following examples, which are provided by way of illustration and are not intended to be limiting of the present invention.

EXAMPLES

Example 1

Materials and Methods

1. Cell Culture and Reagents

Human erythroleukaemic K562 cells (ATCC) were grown in RPMI 1640 medium supplemented with 10% FCS and antibiotics penicillin/streptomycin (Invitrogen). For megakaryocytic differentiation of K562 cultures and unless otherwise specified, cells were treated with 100 ng/ml of TPA (Phorbol 12-myristate 13-acetate, Sigma-Aldrich) for 3 hours, washed twice with PBS and culture in fresh medium for the indicated length of time. For erythrocyte differentiation of K562 cells, hemin (Sigma-Aldrich) was added to the cultures at 100 µg/ml and kept in the medium for the total duration of the experiment. Quantitation of hemoglobin positive cells was performed by the benzidine staining method. Briefly, 200 µl of suspension cells were mixed with 20 µl of freshly prepared benzidine solution (10:1 mixture of 2% 3,3'-dimethoxy-benzidine in 0.5 M acetic acid and 30% hydrogen peroxide). Then the percentage of hemoglobin positive cells, that is cells that stained blue, was calculated using a hemacytometer.

Frozen human umbilical cord blood (CB) CD34+ cells were obtained from StemCell Technologies. Cells were grown in StemSpan H3000 Defined Medium (StemCell Technologies) in the presence of the cytokine cocktail CC200 (containing 50 ng/ml rh Thrombopoietin, 50 ng/ml rh Stem Cell Factor and 10 ng/ml rh IL-3; StemCell Technologies) to drive the differentiation of the hematopoietic precursors to megakaryocytes.

2. miR-Chip Microarrays

Custom microarrays were produced by printing DNA oligonucleotide probes representing 688 miRNAs (Sanger database, version 9 and additional Rosetta validated and predicted miRs). Each probe carries up to 22-nt linker at the 3' end of the miRNA's complement sequence in addition to an amine group used to couple the probes to coated glass slides. 20 µM of each probe were dissolved in 2×SSC+0.0035% SDS and spotted in triplicate on Schott Nexterion® Slide E coated microarray slides using a Genomic Solutions® BioRobotics MicroGrid II according the MicroGrid manufacturer's directions. 64 negative control probes were designed using the sense sequences of different miRNAs. Two groups of positive control probes were designed to hybridize to miRdicator™ array (1) synthetic spikes small RNA were added to the RNA before labeling to verify the labeling efficiency and (2) probes for abundant small RNA (e.g. small nuclear RNAs (U43, U49, U24, Z30, U6, U48, U44), 5.8s and 5s ribosomal RNA) are spotted on the array to verify RNA quality. The slides were blocked in a solution containing 50 mM ethanolamine, 1M Tris (pH 9.0) and 0.1% SDS for 20 mM at 500 C, then thoroughly rinsed with water and spun dry.

15 µg of total RNA was labeled by ligation of a RNA-linker p-rCrU-Cy-dye (Thomson et al., 2004, Nat Methods 1, 47-53) (Dharmacon) to the 3'-end with Cy3 or Cy5. The labeling reaction contained total RNA, spikes (20-0.1 fmoles), 500 ng RNA-linker-dye, 15% DMSO, 1× ligase buffer and 20 units of T4 RNA ligase (NEB) and proceeded at 40 C for 1 hr followed by 1 hr at 370 C. The labeled RNA was mixed with 3× hybridization buffer (Ambion), heated to 95° C. for 3 min and than added on top of the miRdicator™ array. Slides were hybridize 12-16 hr, followed by two washes with 1×SSC and 0.2% SDS and a final wash with 0.1×SSC. The array was scanned using an Agilent Microarray Scanner Bundle G2565BA (resolution of 10 µm at 100% power). The data was analyzed using SpotReader software.

3. RNA Extraction and Northern Blot

Total RNA isolation was performed using Trizol (Invitrogen), according to the manufacturer's instructions. RNA samples (40 µg) were resolved in 15% TBE-Urea acrylamide gels (Invitrogen) and transferred onto Nytran-SPC Nylon Membranes (Whatman) and UV-crosslinked. The membranes were prehybridyzed at 42° C. in 7% SDS/0.2 M sodium phosphate buffer and hybridized at 42° C. with a $\alpha^{32}P$ dATP 3' end labeled oligoprobe against the miRNA of interest. The miRNA probes correspond to DNA oligos (Integrated DNA Technologies, IDT) with a reverse and complementary miRNA sequence. After washing twice at room temperature with 2×SSC/0.1% SDS the membranes were developed using a PhosphorImager (Storm 860, GE Healthcare). As loading control the membranes were also probed with an oligoprobe against snRNA U6.

4. Flow Cytometry and Proliferation Assays

Indirect immunostaining of CD41, CD61, CD49 and glycophorin A cell surface markers was performed using purified mouse monoclonal antibodies (BD Biosciences) as primary reagents and phycoerythrin-conjugated sheep anti-mouse Ab (Caltag) as secondary reagent. Samples were analyzed with a FACSCalibur flow cytometer and CellQuest software (BD Biosciences).

For DNA content analysis, cells were washed once in PBS (Invitrogen), fixed in 70% ethanol at 4° C., washed again in PBS and resuspended in Propidium Iodide staining solution (0.1% (v/v) Triton X-100 in PBS, supplemented with 200 µg/ml of DNase-free RNase A and 20 µg/ml of propidium iodide, Molecular Probes). Samples were incubated at 37° C. for 15 minutes before analysis in a FACSCalibur flow cytometer (BD Biosciences). The data was analyzed using FlowJo (Tree Star, Inc).

Proliferation assays were performed with triplicate samples using the MTT Cell Proliferation Assay (ATCC) according to the manufacturer's instructions.

5. Plasmid DNA Constructs, miRNA Mimics and Transfections miRNA expression plasmids were generated as in (2). Briefly, an approx. 273 by genomic DNA fragment, which includes the mature miRNA sequence, was PCR amplified from genomic DNA extracted from K562 cells using DNeasy kit (Qiagen) and cloned into the BamHI, HindIII restriction sites of pSilencer4.1-CMV-puro (Ambion) using. The vector designated pSilencer4.1-control (Ambion) contains an irrelevant hairpin with no homology to any human or mouse gene. miRNA expression in K562 cells was also achieved using miRIDIAN microRNA Mimics (Dharmacon). The plasmid pCMV6-TP53, encoding the full length cDNA of p53 was obtained from Origene.

The sequence of the promoter region of miR-34a is based on (7) and encompass 1.5 Kb and 0.5 Kb upstream and downstream respectively of the p53BS binding site. This sequence was PCR amplified from genomic DNA extracted from K562 cells and cloned into the restriction sites NheI and XhoI of the promoterless luciferase reporter vector pGL3-basic (Promega). The sequence corresponding to the CD41 promoter has been previously described (8) and was also cloned into pGL3-basic (Promega) using the same restriction sites.

The full length 3'UTR of c-myb was PCR amplified from cDNA generated by RT-PCR from 1 µg of total RNA from K562 cells using Superscript III (Invitrogen). The 3'UTR was then cloned into the XbaI/SalI restriction sites of the luciferase reporter vector pGL3-control (Promega), replacing the SV40 enhancer and SV40 poly(A) signal with the 3'UTR (and poly(A) signal) of the corresponding gene. For testing the rna22-predicted MREs (miRNA response elements, 20-30 nt), sense and antisense oligomers were synthesized, annealed and cloned into psiCHECK-2 (Promega) at restriction sites XhoI & NotI, directly 3' downstream of *Renilla* luciferase.

Short hairpin RNA (shRNA) construct for gene knockdown were generated using the vector pSIREN-RetroQ (Clontech) following the manufacturer's instructions. The siRNAs were designed using Ambion's web tool "siRNA Target Finder". The sequences of the siRNAs used are the following:

```
c-myb shRNA:
sense strand siRNA:
5'GCTTCCAGAAGAACAGTCA3';        [SEQ ID NO: 33]

antisense strand siRNA:
5'TGACTGTTCTTCTGGAAGC3'         [SEQ ID NO: 34]

CDK4 shRNA:
sense strand siRNA:
5'ACGATCAAGGATCTGATGC3';        [SEQ ID NO: 35]

antisense strand siRNA:
5'GCATCAGATCCTTGATCGT3'         [SEQ ID NO: 36]

CDK6 shRNA:
sense strand siRNA:
5'CATGTCGATCAAGACTTGA3';        [SEQ ID NO: 37]

antisense strand siRNA:
5'TCAAGTCTTGATCGACATG3'         [SEQ ID NO: 38]
```

K562 cells were transfected using the nucleofector technology from Amaxa. Cells were transfected using 5 µg of plasmid DNA or 3 µg of miRNA mimic as per manufacturer's protocol.

6. Western Blot

Total cell extracts were prepared in RIPA buffer (50 mM Tris-HCl pH 7.4, 150 mM NaCl, 1 mM EDTA, 1% Triton x-100, 1% Sodium deoxycholate, 0.1% SDS) supplemented with protease inhibitors (1 mM PMSF, 5 µg/ml Aprotinin and 5 µg/ml Leupeptin). Protein concentration was measured using the BCA Protein Assay Reagent (Pierce) and 4 µg of total protein were resolved on 10% SDS-PAGE. The proteins were then transferred to PVDF membranes (Immobilon-P, Millipore) and probed with mouse monoclonal antibodies against c-myb, CDK4 or CDK6 (Cell Signaling Technology) followed by horseradish peroxidase-(HRP) conjugated sheep anti-mouse Ig (Amersham). The membranes were developed using SuperSignal West Femto (Pierce). For loading control the membranes were stripped and reprobed using anti-α-tubulin mouse monoclonal antibody (Sigma-Aldrich).

7. Luciferase Reporter Assays

To perform luciferase assays $7 \times 10^5$ 293T cells per well were plated in a 6-well plate 24 hours before transfection. On the next day, cells were transfected with 500 ng of the Firefly luciferase reporter plasmid pGL3-3'UTR-cMyb, 50 ng of *Renilla* luciferase reporter plasmid pRL-TK (Promega) for control of transfection efficiency and 5 µg of pSilencer4.1_miRNA vector encoding the miRNA of interest. The cells were transfected using Lipofectamine 2000 (Invitrogen) and following the manufacturer's instructions. The luciferase activity was measured 48 hours post-transfection and was normalized to the *Renilla* luciferase activity. The luciferase activity is represented as the percentage of luciferase activity relative to the control (sample transfected with pSilencer4.1-control which contains an irrelevant hairpin).

8. Real-Time PCR Analysis

Analysis of mature miRNA expression was performed using miRNA-specific quantitative real-time PCR (TaqMan MicroRNA Assays; Applied Biosystems). snRNA U6 was used for normalization. Quantitative PCR analysis of the miR-34a targets c-myb, CDK4 and CDK6 was performed by SYBR Green real-time PCR analysis (Applied Biosystems). In this case samples were normalized to GAPDH. The primers used for SYBR Green real-time PCR analysis were obtained from Primer Bank and their sequence is indicated below:

```
GAPDH fw:
5'CATGAGAAGTATGACAACAGCCT3'     [SEQ ID NO: 39]

GAPDH rv:
5'AGTCCTTCCACGATACCAAAGT3'      [SEQ ID NO: 40]

c-Myb fw:
5'AAGGGGACAGTCTGAATACCC3'       [SEQ ID NO: 41]

c-Myb rv:
5'AGGTTCCCAGGTACTGCTACA3'       [SEQ ID NO: 42]

CDK4 fw:
5'GATCTGATGCGCCAGTTTCTAA3'      [SEQ ID NO: 43]

CDK4 rv:
5'ACTGTTCCACCACTTGTCACC3'       [SEQ ID NO: 44]

CDK6 fw:
5'CAGATGGCTCTAACCTCAGTGG3'      [SEQ ID NO: 45]

CDK6 rv:
5'CACGAAAAAGAGGCTTTCTACGA3'     [SEQ ID NO: 46]
```

Example 2 miRNA Signature of TPA-Induced Megakaryocyte Differentiated K562 Cells

To explore the role of miRNAs during differentiation of leukemic K562 cells, we analyzed miRNA expression in undifferentiated vs. TPA-induced MK differentiated cells using miR-chip microarrays. Total RNA was extracted from untreated K562 cells or from cells cultured for 2 or 4 days after TPA treatment, at which time they stop proliferating, become adherent and express megakaryocyte markers (not shown). cRNA was generated and hybridized onto chips containing probes for 461 annotated miRNAs as described. Results from this experiment showed that total miRNA expression increased upon differentiation and that 67 miRNAs were upregulated >=1.5 fold in TPA-differentiated K562 cells. Among the strongest upregulated miRNAs were miR-34a (SEQ ID NO: 2), miR-139 (SEQ ID NO: 10), and the miRNA clusters miR-132 (SEQ ID NO: 4)/miR-212 (SEQ ID NO: 11), miR-181a (SEQ ID NO: 1)/miR-181b (SEQ ID NO: 9) and miR-221 (SEQ ID NO: 6)/miR-222 (SEQ ID NO: 5) (FIGS. 1A and B, Table 1). The miR-chip microarray data was validated by northern blot (FIG. 1B). These experiments further validated the upregulation of other miRNAs such as miR-134 (SEQ ID NO: 7), miR-375 (SEQ ID NO: 3), miR-299-5p (SEQ ID NO: 12) and miR-409-3p (SEQ ID NO: 8) with lower but significant fold increase in the miR-chip array (FIG. 1B). In addition, several miRNAs were also significantly downmodulated, including miR-218 and the miRNA clusters miR-17-5p/18a/20a and miR-106a/19b/92 (FIGS. 1A and B). Importantly, the miRNAs upregulated in TPA-treated K562 cells seem to be specific to the megakaryocytic pathway since none of these miRNAs is upregulated during hemin-induced erythroid differentiation of K562 cells (FIG. 1C).

TABLE 1

Sequences of the miRNAs and their predicted binding sites

| microRNA | Sequence of the predicted binding site | SEQ ID NO: | Sequence of the microRNA | SEQ ID NO: |
|---|---|---|---|---|
| hsa-miR-181a | CACCAAGTGCATTTAGTTGAATG | 13 | AACATTCAACGCTGTCGGTGAGT | 1 |
| hsa-miR-34a | cTTAGCCTGTAGACATGCTGCTA | 14 | TGGCAGTGTCTTAGCTGGTTGTT | 2 |
| hsa-miR-375 | GGGGCAGTAGAGCTTGGACAGA | 15 | TTTGTTCGTTCGGCTCGCGTGA | 3 |
| hsa-miR-181a | TTCTATGTTttgttttgAGTGTA | 16 | AACATTCAACGCTGTCGGTGAGT | 1 |
| hsa-miR-132 | tttgAGTGTAGCCTGACTGTTt | 17 | TAACAGTCTACAGCCATGGTCG | 4 |
| hsa-miR-222 | ACTGGGGAGACAGAAACTGTGGTT | 18 | AGCTACATCTGGCTACTGGGTCTC | 5 |
| hsa-miR-221 | CTGGGGAGACAGAAACTGTGGTT | 19 | AGCTACATTGTCTGCTGGGTTTC | 6 |
| hsa-miR-134 | CTGTGGTTGATAGCCAGTCAC | 20 | TGTGACTGGTTGACCAGAGGG | 7 |
| hsa-miR-34a | TGGTTGATAGCCAGTCACTGCCT | 21 | TGGCAGTGTCTTAGCTGGTTGTT | 2 |
| hsa-miR-34a | agtgAGcAAtggAGTggctgcca | 23 | TGGCAGTGTCTTAGCTGGTTGTT | 2 |
| hsa-miR-34a | AAAACCTGGATTCCCAcCTGccg | 24 | TGGCAGTGTCTTAGCTGGTTGTT | 2 |
| hsa-miR-34a | GGAAACCGCCTAGTTTACTGTTT | 25 | TGGCAGTGTCTTAGCTGGTTGTT | 2 |
| hsa-miR-34a | ATGTAATCTctCTGcagctgccg | 26 | TGGCAGTGTCTTAGCTGGTTGTT | 2 |
| hsa-miR-34a | GTACTTTCTGCCACACACTGCCT | 27 | TGGCAGTGTCTTAGCTGGTTGTT | 2 |
| hsa-miR-34a | ACACAGATTGCTATAAACTGTTA | 28 | TGGCAGTGTCTTAGCTGGTTGTT | 2 |
| hsa-miR-34a | ACAACATTGATTAGGTGttgtcA | 29 | TGGCAGTGTCTTAGCTGGTTGTT | 2 |
| hsa-miR-34a | CCAGTACAAGAATGTCCCTGCTA | 30 | TGGCAGTGTCTTAGCTGGTTGTT | 2 |
| hsa-miR-34a | GAGCATCTGCTGAAATACTGTTA | 31 | TGGCAGTGTCTTAGCTGGTTGTT | 2 |
| hsa-miR-34a | gtaTTAGTGTTTCTGCATTGCCA | 32 | TGGCAGTGTCTTAGCTGGTTGTT | 2 |
| hsa-miR-409-3p | AGTCACTGCCTTAAGAACATTtG | 22 | CGAATGTTGCTCGGTGAACCCCT | 8 |
| hsa-miR-181b | | | AACATTCATTGCTGTCGGTGGG | 9 |
| hsa-miR 139 | | | TCTACAGTGCACGTGTCT | 10 |
| hsa-miR 212 | | | TAACAGTCTCCAGTCACGGCC | 11 |
| hsa-miR 299-5p | | | TGGTTTACCGTCCCACATACAT | 12 |

Example 3 miRNA 34a Promotes Megakaryocytic Differentiation of Leukemic K562 Cells

Figure 2A:
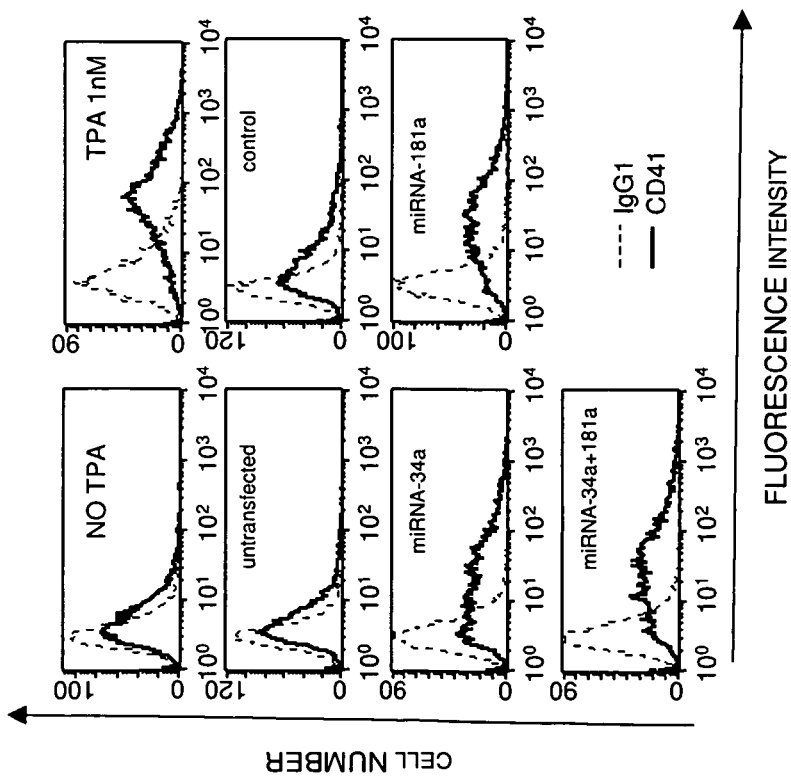

Differentiation of K562 cells with phorbol esters to MKs is characterized by increased size, adherence, cell cycle arrest, and expression of MK markers, such as the gpIIb/IIIa integrin (CD41/CD61). To test the hypothesis that miRNAs upregulated in TPA-differentiated K562 cells play an important role in their terminal differentiation, we evaluated the effect that miRNA overexpression had on cell proliferation and expression of MK markers. Undifferentiated K562 cells were transfected with miRNA mimics corresponding to each of the upregulated miRNAs or a control miRNA mimic containing an irrelevant sequence. 48 hours post-transfection cells were treated with a suboptimal amount of TPA (0.1 nM), which is low enough not to induce differentiation of untransfected or mimic control transfected K562 cells (FIG. 2A). MK differentiation was assessed by flow cytometry analysis of CD41 and CD61 expression (FIG. 2A and data not shown). As shown in FIG. 2A overexpression of miRNAs 34a and 181a in undifferentiated K562 cells induced upregulation of CD41 when the cells were treated with a suboptimal amount of TPA. No significant upregulation of the CD41 integrin was observed in duplicate samples not treated with 0.1 nM TPA (not shown). Furthermore, no cooperative effect in CD41 upregulation was seen when a combination of all selected miRNAs was transfected into undifferentiated K562 cells (not shown).

Figure 3:
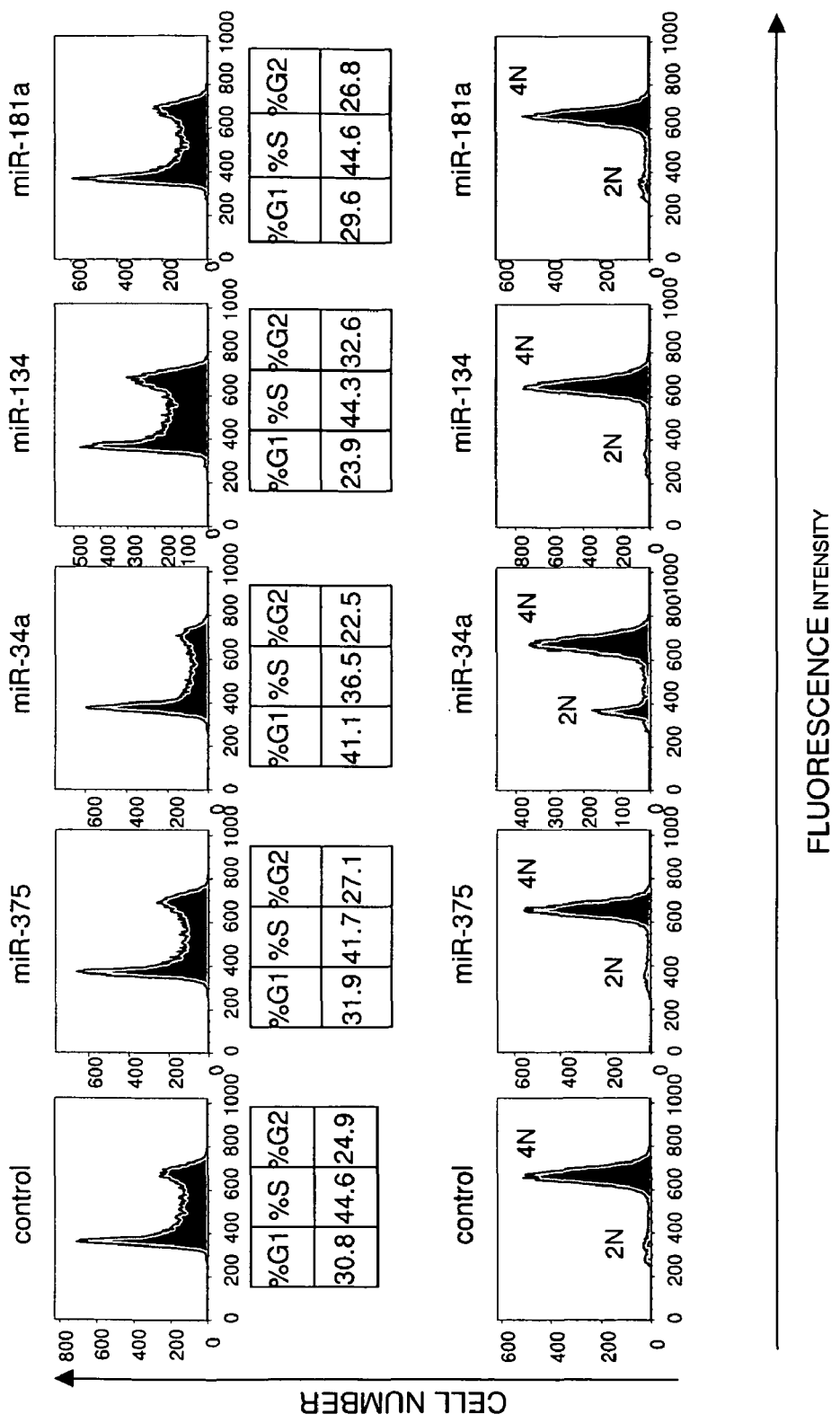
FIG. 3 shows that miRNAs 34a (SEQ ID NO: 2) and 134 (SEQ ID NO: 7) alter cell cycle progression in leukemic K562 cells. K562 cells were transfected with the indicated miRNA mimic or a mimic control as described above. 48 h post transfection cells were collected and DNA content of propidium iodide stained cells was analyzed by flow cytometry. Replicate samples were either left untreated (upper) or treated with nocodazole (lower) (100 ng/ml) for 16 hours before propidium iodide staining The percentage of cells in the G1, S or G2 phase of the cell cycle is indicated. 2N designates cells with a diploid DNA content and 4N designates a tetraploid DNA content.

We also evaluated the effect of miRNA overexpression on cell proliferation and cell cycle regulation. As shown in FIG. 2B, overexpression of miRNAs 34a and 134 inhibited cell proliferation upon treatment of transfected K562 cells with a suboptimal amount of TPA (0.1 nM). Overexpression of miR-181a also caused a reduction in cell proliferation although the inhibition was not as pronounced as for miR-34a or miR-134 (data not shown). To further understand how these miRNAs control cell proliferation during TPA-induced MK differentiation of K562 cells we performed cell cycle analysis in miRNA overexpressing K562 cells. As shown in FIG. 3, miR-34a overexpression induced a significant reduction of cells in the G2/S phase of the cell cycle and a corresponding increase of cells in the G1 phase. Accordingly, there is a significant increase of cells in 2N when the cells are pre-treated with nocodazole for 16 hours previous to propidium iodide analysis (FIG. 3, bottom panel). Interestingly, miR-134 causes a decrease of cells in G1 and a corresponding increase of cells in the G2/S phase of the cell cycle. No alteration of the cell cycle profiled was observed for miRNAs 181a or 375 as compared to control transfected cells. Taken together, these results suggest that miRNAs 34a, 181a and 134 play crucial roles during the process of terminal differentiation of leukemic K562 cells to megakaryocytes.

Example 4 miR-34a Regulates the Expression of the Transcription Factor c-myb and of Key Cell Cycle Regulators CDK4 and CDK6

Figure 4B:
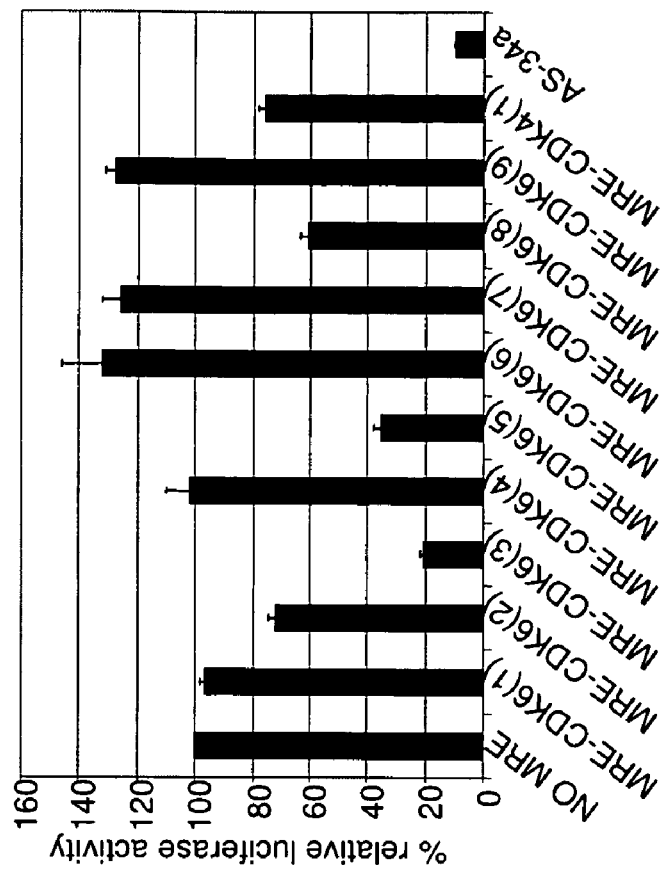
FIG. 4 show that miR-34a directly regulates the expression of c-myb, CDK4 and CDK6. (A). Analysis of miR-34a overexpression on the luciferase activity of a reporter vector containing either the full length 3'UTR of c-myb or individual rna22-predicted MREs (miRNA response elements). 293T cells were transfected with a Firefly luciferase reporter plasmid containing the full length cMyb 3'UTR, a *Renilla* luciferase reporter plasmid for control of transfection efficiency and pSilencer4.1_miRNA encoding the miRNA of interest (top panel). The luciferase activity was measured 48 hours post-transfection and was normalized to the *Renilla* luciferase activity. The luciferase activity is represented as the percentage of luciferase activity relative to the control (transfection with pSilencer4.1_control which contains an irrelevant hairpin). For the analysis of the predicted miR34a MREs in the 3'UTR of c-myb, sense and antisense oligomers were annealed and cloned into psiCHECK2 directly 3' downstream of *Renilla* luciferase. Cells were transfected with psiCHECK2-MRE and pSilencer4.1_miR-34 as described above. Luciferase activity was measured 48 hours post-transfection and in this case the luciferase activity was normalized to the Firefly luciferase activity. The diagram represents the percentage of luciferase activity relative to the control (psiCHECK2 vector with no MRE). (B). Analysis of CDK4 and CDK6 miR-34a predicted MREs. Analysis of CDK4 and CDK6 rna22-predicted MREs was performed as described above. (C). Overexpression of miR-34 in K562 cells induces downregulation of c-myb, CDK4 and CDK6 protein levels. K562 cells were transfected with the indicated miRNA mimic or a mimic control and c-myb, CDK4 and CDK6 protein levels were determined by immunoblot analysis of cell lysates prepared 48 hours post transfection. For loading control the membranes were stripped and reprobed with a MAb against α-tubulin. (D). Overexpression of miR-34 in K562 cells induces downregulation of c-myb, CDK4 and CDK6 m-RNA levels. K562 cells were transfected as described above and total RNA was prepared 48 hours post transfection using Trizol and according to the manufacturer's instructions. cDNA was generated using Superscript III (Invitrogen) and mRNA levels were evaluated performing quantitative SYBR Green Real-Time PCR analysis. Samples were normalized to the housekeeping gene GAPDH and results were plotted as fold difference expression relative to the control (K562 cells transfected with a miRNA MIMIC control).
Figure 4A:
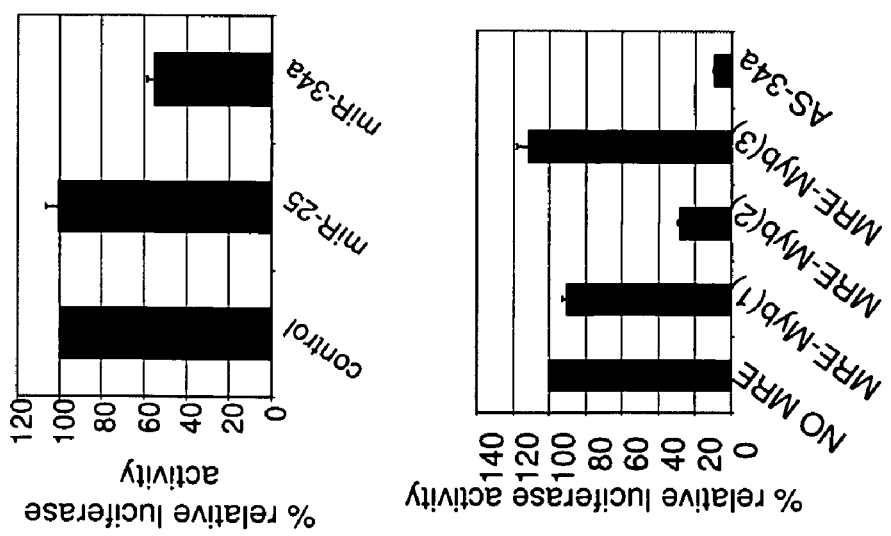

To better understand the role of the upregulated miRNAs during MK differentiation, we analyzed what genes or regulatory networks were regulated by these miRNAs, focusing in particular on miR-34a, since this miRNA seemed to have a broader impact on the differentiation process. In silico analysis of miR-34a targets using the recently developed algorithm Rna22 (5), revealed that the transcription factor c-myb was a putative target of miR-34a (SEQ ID NOs: 14, 21). c-myb is an important regulator of hematopoietic cell differentiation and its mRNA and protein were significantly down-regulated following TPA treatment of K562 cells as analyzed by Northern blot and immunoblot respectively (not shown). To prove that c-myb is directly regulated by miR-34a we cloned the full length 3'UTR of c-myb in a luciferase reporter plasmid and evaluated the effect that miR-34a overexpression had on the luciferase activity. As shown in FIG. 4A (top panel) overexpression of miR-34a caused a 45% reduction of the luciferase activity in relation to the control. Overexpression of miR-25, which does not target c-myb according to Rna22 and whose expression does not change during TPA-induced differentiation did not modify the luciferase activity. We also, analyzed the three predicted MREs (miRNA Response Elements) in luciferase assays. The results from these experiments showed that c-myb MRE(2) caused a 70% reduction of the luciferase activity of the reporter vector in the presence of miR-34a (FIG. 4A, bottom panel). This reduction was almost as strong as the reduction obtained when a perfect match sequence was cloned in the luciferase vector (90% reduction as shown in FIG. 4A bottom). Mutation of the seed in the MRE(2) of c-myb caused an increase of the luciferase activity, although this restoration was not complete. This may suggest that MRE(1) may have a stronger effect in the context of the full length 3'UTR or that other binding sites no predicted by Rna22 may be also contributing to the inhibition. To further demonstrate that c-myb is a target of miR-34a we overexpressed miR-34a in undifferentiated K562 cells and analyzed c-myb protein levels in transfected cells. As shown in FIG. 4C miR-34a overexpression caused a significant reduction in c-myb protein levels as compared to the control. Also as control are shown miR-375 and miR-181a which do not alter c-myb levels (FIG. 4C).

Bioinformatics analysis of miR-34a targets also revealed additional genes with important roles in cell cycle regulation such as CDK4 and CDK6. As for c-myb, it has also been described that the mRNA and protein levels of CDK4 and CDK6 are dowregulated during TPA-induced MK differentiation of K562 cells (references and suppl. data). The Rna22-predicted miR-34a MREs are listed on table 1. Analysis of the ability of miR-34a to inhibit the activity of a luciferase reported vector in which these predicted MREs were individually cloned revealed that CDK6 MREs 3 and 5 strongly reduced the luciferase activity (80 and 65% respectively, FIG. 4B) while MREs 2 and 8 had a moderate effect (25 and 40% respectively). The only predicted CDK4 MRE had a moderate effect, 20% reduction, although the effect was consistently reproducible. In addition, miR-34a overexpression in undifferentiated K562 cells significantly reduced CDK4 and CDK6 protein levels (FIG. 4C). Overexpression of miR-299-5p, which does not target either gene, did not modify CDK4 or CDK6 levels (FIG. 4C).

Figure 4D:
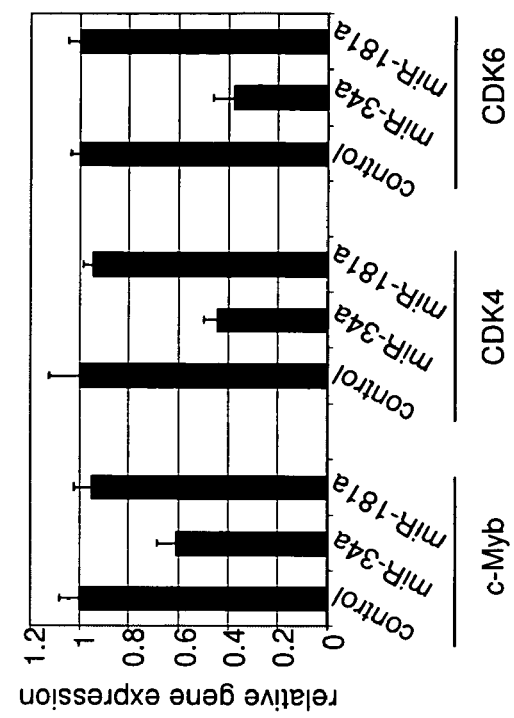
Figure 4C:
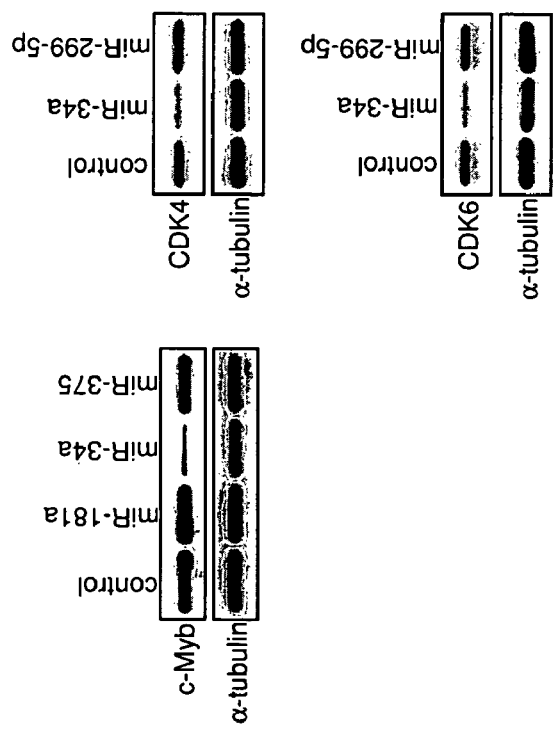

Last, it is worth mentioning that regulation of the analyzed miR-34a targets seems to be performed at the RNA level since overexpression of miR-34a in undifferentiated K562 cells caused a significant reduction of c-myb, CDK4 and CDK6 mRNA levels as analyzed by Real-Time PCR (FIG. 4D).

Example 5

Concomitant Reduction of CDK4 and CDK6 Proteins is Required for Inhibition of Proliferation in Leukemic K562 Cells To evaluate whether miR-34a regulates TPA-induced MK differentiation of K562 cells through inhibition of the targets identified by bioinformatics analysis, we used RNA interference to evaluate the effect that c-myb or CDK4/CDK6 knockdown had on cell proliferation and on the expression of the MK specific marker CD41. As shown in FIG. 5A, knockdown of c-myb with shRNA induces a significant upregulation of CD41 expression in untreated K562 cells as measured by flow cytometry. In addition, treatment of shRNA transfected K562 cells with a suboptimal amount of TPA (0.1 nM) caused a further increased in CD41 expression. Notably, the magnitude of CD41 increase was comparable to the one obtained when miR-34a is overexpressed in K562 cells (FIG. 2A).

Similarly, we used shRNAs to knockdown CDK4 and CDK6 and evaluate its effect on cell proliferation and cell cycle. Interestingly, knocking down CDK4 or CDK6 individually had no significant effect on proliferation of K562 cells (FIG. 5B, top right panel), however when both proteins were knocked down simultaneously the rate of proliferation decreased significantly.

Similarly, individual knock down of CDK4 or CDK6 did not greatly altered the cell cycle profile of shRNA transfected K562 cells, although in CDK6 KD cells there was a small but significant decreased of cells in G2/S and a corresponding increase of cells in G1 (37.9% in CDK6 KD cells vs. 27.8% in control cells). However, when CDK4 and CDK6 were simultaneously knocked down there was a dramatic increased of cells in G1 (69.9%) and a corresponding decrease of cells in G2/S (29.2% in CDK4/CDK6 KD cells vs. 72.2% in control cells) (FIG. 5B, bottom panel). The result of these experiments are consistent with previous work showing that CDK4 and CDK6 have redundant roles in the control of the cell cycle and highlight the relevance of miR-34a as a regulator of both kinases.

Example 6 miR-34a Upregulation in TPA-Differentiated K562 Cells is p53 Independent

Several groups have recently shown that miR-34a is directly activated at the transcriptional level by the tumor suppressor p53 and that in turn miR-34a regulates the expression of numerous genes that have previously shown to be regulated by p53 (1, 3, 7, 10), highlighting the relevance of miR-34a as part of the p53 regulatory network. However, it is well established that leukemic K562 cells are p53 null cells (4) and therefore they have often been used as a model to study p53 function. K562 cells contain a single cytosine insertion in exon 5, between codons 135 and 136, which generate a frameshift mutation leading to an N-terminal truncated protein of 147 amino acids. Importantly, although a shorter transcript can be detected by RT-PCR in K562 cells neither the truncated nor the full length proteins are detected by western blot (4).

miR-34a is contained within the second exon of an EST (expressed sequence tag; accession number DB286351) encoded by the negative strand of human chromosome 1. Exon 1 is separated from exon2 by an intron of about 30 Kb and contains a p53 binding site that is conserved across species and that is responsible for p53 transactivation of miR-34a (1, 2, 7). We first analyzed whether the primary transcript was upregulated during TPA-induced megakaryocytic differentiation of K562 cells. Thus, we performed semiquantitative RT-PCR using primers spanning the boundary of exons 1 and 2. The results of these experiments showed that the primary transcript was not expressed in undifferentiated K562 cells but its expression was induced upon treatment of K562 cells with TPA (sppl. data) Importantly, this data is in agreement with the expression pattern of miR-34a during MK differentiation of K562 cells (FIG. 1B).

To further demonstrate that the upregulation of the primary transcript during TPA-induced differentiation is p53 independent, we cloned the putative promoter into the promoter-less luciferase reporter vector pGL3-basic and evaluated the effect of TPA treatment on the luciferase activity. As shown in FIG. 6A, there is no significant increase in luciferase activity in the reporter construct containing the putative miR-34a promoter. As comparison, a reporter vector in which the luciferase gene is under control of the TPA-responsive CD41 promoter gave a 400 fold increase in luciferase activity (FIG. 6A). Most importantly, the luciferase activity of the putative miR-34a promoter reporter vector is strongly activated (100 fold increase relative to promoter less reporter vector) when the reporter is cotransfected with a plasmid encoding for p53 (FIG. 6B). Also, in agreement with previous reports p53 is undetectable in untransfected or control transfected cells (FIG. 6B, bottom panel).

Taken together, these results clearly demonstrate the p53 independence of miR-34a upregulation during TPA-induced megakaryocytic differentiation of leukemic K562 cells. In addition, our data also suggest that DNA regulatory sequences other than the ones contained in the putative described miR-34a promoter might be responsible for TPA-induced miR-34a activation in leukemic K562 cells.

Figure 7A:
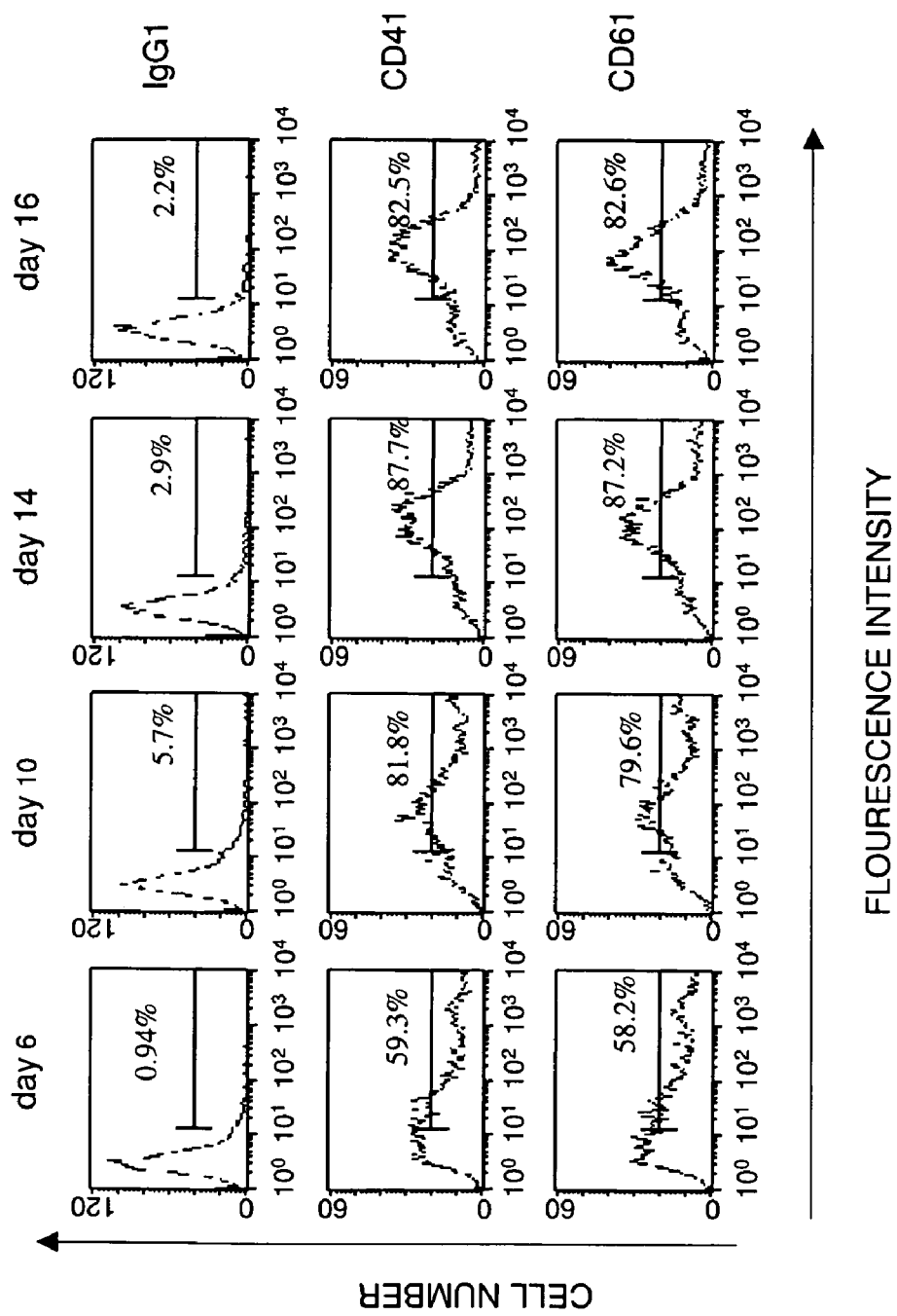
FIG. 7 shows analysis of miR-34a expression in MKs expanded from human CD34+ cells ex vivo. Human CD34+ progenitor cells were differentiated ex vivo to megakaryocytes culturing the cells in the presence of 50 ng/ml rh Thrombopoietin, 50 ng/ml rh Stem Cell Factor and 10 ng/ml rh IL-3 for 16 days. (A). The percentage of megakaryocytic differentiated cells was determined by flow cytometry analysis of CD41/CD61 positive cells at the indicated time points (B). Expression levels of miR-34a and its targets c-myb and CDK4 were evaluated by Real-Time PCR analysis of RNA samples extracted at the indicated time points during differentiation.
Figure 7B:
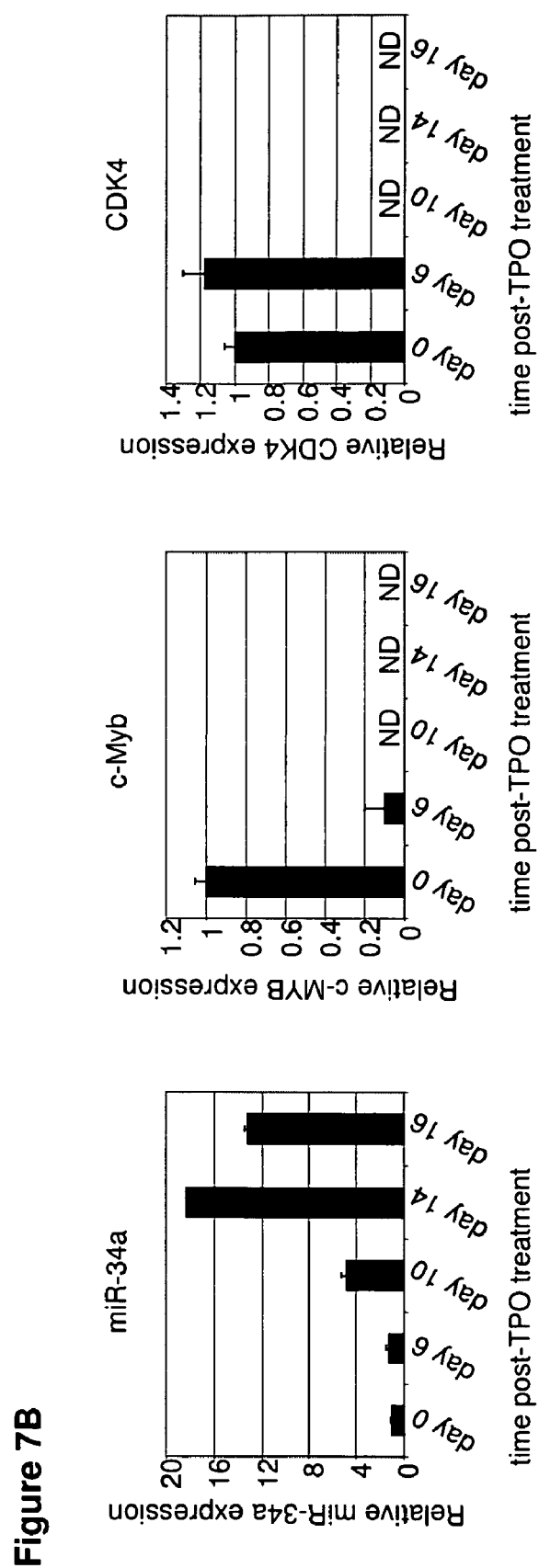

Example 7 miRNA-34a is Upregulated During Thrombopoietin (TPO)-Induced Megakaryocytic Differentiation of Primary Human CD34+Cells miRNAs upregulated by in vitro differentiation in leukemia cell lines may provide important information about what blocks terminal differentiation in leukemic cells. However, this information can only be properly evaluated in the context of knowledge about miRNA expression during differentiation of primary hematopoietic precursor cells. To address this issue, we analyzed miR-34a expression in MKs derived from ex vivo expanded CD34+ hematopoietic precursors. Thus, we differentiated human primary CD34+ cells into MKs by culturing them in the presence of thrombopoietin, IL-3 and stem cell factor. The yield of mature MKs was determined by FACS staining using antibodies against the MK specific markers CD41 and CD61 (FIG. 7A). Total RNA was extracted from these cells at different time points during differentiation and miR-34a expression was analyzed using quantitative Real-Time PCR. As shown in FIG. 7B miR-34a expression is increased upon MK differentiation of CD34+ hemotopietic precursors. Interestingly, miR-34a expression is inversely correlated to the expression of its targets c-myb, CDK4 and CDK6 (FIG. 7B).

Example 8

In Vivo Protocol for Evaluating the Role of miR-34a as a Tumor Suppressor

We have developed an efficient and highly specific method for delivering siRNAs in vivo (9). This method is based on the use of an antibody-protamine fusion protein which specifically delivers siRNAs to cells expressing the targeted receptor. Using the fusion protein F105-P which contains the protamine sequence fused to the heavy chain Fab fragment of an HIV-1 envelope antibody, efficient inhibition of melanoma growth was achieved in vivo when siRNAs against c-myc, MDM2 or VEGF were delivered to B16 tumor cells bearing the gp160 receptor either locally by intratumoral injection or systemically by intravenous injection (9). We also have demonstrated that an antibody-protamine fusion protein targeting human LFA-1 (lymphocyte function-associated antigen-1) efficiently delivers siRNAs to lymphocytes and other primary blood cells that are difficult to target in vivo. Using this protamine fusion protein we showed efficient in vivo delivery of a fluorophore-conjugated siRNA to K562 cells bearing the human LFA-1 antigen and engrafted in the lungs of SCID mice (6). Delivery of siRNAs using antibody-protamine fusion proteins is a powerful tool for in vivo gene silencing and has a great potential as a therapeutic approach.

To evaluate the in vivo relevance of miR-34a as a tumor suppressor taking advantage of the system that we have developed for specific in vivo delivery of siRNAs using the LFA-1 antibody-protamine fusion protein. We are using this fusion protein for delivering miR-34a to leukemic K562 cells stably expressing the LFA-1 antigen and engrafted in SCID mice and evaluate its effect in tumor growth in those mice.

Initially, we are performing in vitro experiments to optimize the conditions for efficient delivery of miRNAs to LFA-1 expressing K562 cells. As miRNA mimics we are using double stranded RNAs chemically modified to exclude loading of the passenger strand into the RISC complex. These miRNA mimics are conjugated to the LFA-1 antibody-protamine fusion protein at different molar ratios in 50 µl of PBS, preincubated for 30 minutes at room temperature and then added to $2 \times 10^5$ parental or LFA-1 expressing K562 cells in 150 µl of RPMI medium 1640/10% FCS in the presence of 1 mM $MgCl_2/CaCl_2$. Cells are cultured for 6-72 hours at 37° C., 5% CO2 and then subjected to functional studies. An antibody-protamine fusion protein targeting a membrane receptor not expressed in K562 cells, a single chain antibody fragment (scFv) or protamine alone serve as negative controls. The ability of miR-34a, delivered using the LFA-1 antibody-protamine fusion protein, to induce MK differentiation of K562 cells are determined by flow cytometry analysis of the megakaryocytic specific marker CD41 after 2 days post treatment with a suboptimal amount of TPA (0.1 nM). In addition, the proliferation ability of the transduced cells are evaluated using the MTT assay (ATCC) and the cell cycle profile is determined by flow cytometry analysis of cells stained with propidium iodide. These results will be compared to the ones obtained from K562 cells transfected with the corresponding miRNA mimic using the nucleofection technology from Amaxa and analyzed in parallel.

Once we have validated our experimental system in vitro, we will evaluate the ability of miR-34a to interfere with tumor growth in an in vivo model. In a first set of experiments and using the LFA-1 antibody-protamine fusion protein we will deliver miR-34a or a control miRNA to parental or LFA-1 expressing K562 cells in vitro. Then, the tumorigenic potential of these cells will be evaluated in vivo by introducing $6 \times 10^6$ cells into 5-7 weeks old SCID mice (Charles River Breeding Laboratory, Wilmington, Mass.) by tail vein injection. Three weeks after inoculation mice will be sacrificed and organs and tumors will be dissected for further analysis. In a second set of experiments parental or LFA-1 expressing K562 cells will be first introduced into SCID mice as mentioned above and two weeks post inoculation miR-34a or control mimic complexed with fusion protein in 100 µl of PBS will be inoculated by tail vein injection. Mice will be sacrificed at different times post-injection, and the metastatic lesions in different organs will be analyzed. Last, in a third set of in vivo experiments the mice will be treated as described above and their survival will be evaluated over time. If miR-34 mimics by themselves do not have a substantial impact on tumor outgrowth or survival, we will also investigate combining miR-34 therapy with chemotherapy drugs such as cyclophosphamide.

REFERENCES

1. Chang, T. C., E. A. Wentzel, O. A. Kent, K. Ramachandran, M. Mullendore, K. H. Lee, G. Feldmann, M. Yamakuchi, M. Ferlito, C. J. Lowenstein, D. E. Arking, M. A. Beer, A. Maitra, and J. T. Mendell. 2007. Transactivation of miR-34a by p53 broadly influences gene expression and promotes apoptosis. Mol Cell 26:745-52.
2. Chen, C. Z., L. Li, H. F. Lodish, and D. P. Bartel. 2004. MicroRNAs modulate hematopoietic lineage differentiation. Science 303:83-6.
3. He, L., X. He, L. P. Lim, E. de Stanchina, Z. Xuan, Y. Liang, W. Xue, L. Zender, J. Magnus, D. Ridzon, A. L. Jackson, P. S. Linsley, C. Chen, S. W. Lowe, M. A. Cleary, and G. J. Hannon. 2007. A microRNA component of the p53 tumour suppressor network. Nature 447:1130-4.
4. Law, J. C., M. K. Ritke, J. C. Yalowich, G. H. Leder, and R. E. Ferrell. 1993. Mutational inactivation of the p53 gene in the human erythroid leukemic K562 cell line. Leuk Res 17:1045-50.
5. Miranda, K. C., T. Huynh, Y. Tay, Y. S. Ang, W. L. Tam, A. M. Thomson, B. Lim, and I. Rigoutsos. 2006. A pattern-based method for the identification of MicroRNA binding sites and their corresponding heteroduplexes. Cell 126:1203-17.
6. Peer, D., P. Zhu, C. V. Carman, J. Lieberman, and M. Shimaoka. 2007. Selective gene silencing in activated leukocytes by targeting siRNAs to the integrin lymphocyte function-associated antigen-1. Proc Natl Acad Sci USA 104:4095-100.
7. Raver-Shapira, N., E. Marciano, E. Meiri, Y. Spector, N. Rosenfeld, N. Moskovits, Z. Bentwich, and M. Oren. 2007. Transcriptional activation of miR-34a contributes to p53-mediated apoptosis. Mol Cell 26:731-43.
8. Sevinsky, J. R., A. M. Whalen, and N. G. Ahn 2004. Extracellular signal-regulated kinase induces the megakaryocyte GPIIb/CD41 gene through MafB/Kreisler. Mol Cell Biol 24:4534-45.
9. Song, E., P. Zhu, S. K. Lee, D. Chowdhury, S. Kussman, D. M. Dykxhoorn, Y. Feng, D. Palliser, D. B. Weiner, P. Shankar, W. A. Marasco, and J. Lieberman. 2005. Antibody mediated in vivo delivery of small interfering RNAs via cell-surface receptors. Nat Biotechnol 23:709-17.
10. Tarasov, V., P. Jung, B. Verdoodt, D. Lodygin, A. Epanchintsev, A. Menssen, G. Meister, and H. Hermeking. 2007. Differential regulation of microRNAs by p53 revealed by massively parallel sequencing: miR-34a is a p53 target that induces apoptosis and G1-arrest. Cell Cycle 6:1586-93.
11. Wang, X., Seed, B. 2003. A PCR primer bank for quantitative gene expression analysis. Nucleic Acid Res. 31: e154

The invention claimed is:

1. A method for treating an in vivo or ex vivo hematologic neoplasm comprising administering to a subject in need thereof or to cells harvested from said subject an effective amount of a composition comprising a nucleic acid sequence selected from the group consisting of:
   (a) SEQ ID NO: 2;
   (b) a DNA encoding (a), wherein the DNA is identical in length to (a);
   (c) a sequence at least 80% identical to (a) or (b);
   (d) a complement of any one of (a)-(c), wherein the complement is identical in length to (a) or (c); and
   (e) the nucleic acid of any one of (a)-(d) comprising a 2'-O-methyl group.

2. The method of claim 1, wherein the hematologic neoplasm is selected from the group consisting of: chronic myeloid leukemia, acute myeloid leukemia, acute lymphatic leukemia, chronic lymphatic leukemia, erythroleukemia, myeloproliferative syndromes, polycythemia vera, essential thrombocytosis, myelodysplastic syndromes, cutaneous T-Cell lymphoma, hairy cell leukemia, Hodgkin's lymphoma, non-Hodgkin's lymphoma and plasma cell neoplasms.

3. A method for inducing suppression of lymphocyte proliferation comprising administering to a subject in need thereof or to cells harvested from said subject an effective amount of a composition comprising a nucleic acid sequence selected from the group consisting of:
   (a) SEQ ID NO: 2;
   (b) a DNA encoding (a), wherein the DNA is identical in length to (a);
   (c) a sequence at least 80% identical to (a) or (b);
   (d) a complement of any one of (a)-(c), wherein the complement is identical in length to (a) or (c); and
   (e) the nucleic acid of any one of (a)-(d), comprising a 2'-O-methyl group.

4. A method of modulating the expression level of c-myb, CDK4 or CDK6 comprising introducing to a subject in need thereof an effective amount of a composition comprising a nucleic acid sequence selected from the group consisting of:
   (a) SEQ ID NO: 2;
   (b) a DNA encoding (a), wherein the DNA is identical in length to (a);
   (c) a sequence at least 80% identical to (a) or (b);
   (d) a complement of any one of (a)-(c), wherein the complement is identical in length to (a) or (c); and
   (e) the nucleic acid of any one of (a)-(d), comprising a 2'-O-methyl group.

5. A method for treating a hematologic neoplasm comprising administering to a subject thereof an effective amount of a composition comprising a nucleic acid sequence selected from the group consisting of:
   (a) SEQ ID NO: 2;
   (b) a DNA encoding (a), wherein the DNA is identical in length to (a);
   (c) a sequence at least 80% identical to (a) or (b);
   (d) a complement of any one of (a)-(c), wherein the complement is identical in length to (a) or (c); and
   (e) the nucleic acid of any one of (a)-(d), comprising a 2'-O-methyl group.

6. The method of claim 5, wherein the hematologic neoplasm is treated ex vivo or in vivo.

7. The method of claim 5, wherein the hematologic neoplasm is selected from the group consisting of: relapsed Hodgkin's disease, resistant Hodgkin's disease high grade, low grade and intermediate grade non-Hodgkin's lymphomas, B cell chronic lymphocytic leukemia (B-CLL), lymhoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, angioimmunoblastic lymphoadenopathy, small lymphocytic; follicular, diffuse large cell; diffuse small cleaved cell; large cell immunoblastic lymphoblastoma; small, non-cleaved; Burkitt's and non-Burkitt's; follicular, predominantly large cell; follicular, predominantly small cleaved cell; and follicular, mixed small cleaved and large cell lymphomas.

8. The method of claim 5, further comprising administering at least one additional therapy.

9. The method of claim 8, wherein the at least one additional therapy is a chemotherapeutic agent.

10. The method of claim 8, wherein the chemotherapeutic agent is selected from the group consisting of 5-fluorouracil, doxorubicine, mitomycin c, etoposide, carboplatin, and cyclophosphamide.

* * * * *

SEQUENCE LISTING

<160> NUMBER OF SEQ ID NOS: 46

<210> SEQ ID NO 1
<211> LENGTH: 23
<212> TYPE: RNA
<213> ORGANISM: Homo sapiens

<400> SEQUENCE: 1
aacauucaac gcugucggug agu                                              23

<210> SEQ ID NO 2
<211> LENGTH: 23
<212> TYPE: RNA
<213> ORGANISM: Homo sapiens

<400> SEQUENCE: 2
uggcaguguc uuagcugguu guu                                              23

<210> SEQ ID NO 3
<211> LENGTH: 22
<212> TYPE: RNA
<213> ORGANISM: Homo sapiens

<400> SEQUENCE: 3
uuuguucguu cggcucgcgu ga                                               22

<210> SEQ ID NO 4
<211> LENGTH: 22
<212> TYPE: RNA
<213> ORGANISM: Homo sapiens

<400> SEQUENCE: 4
uaacagucua cagccauggu cg                                               22

<210> SEQ ID NO 5
<211> LENGTH: 24
<212> TYPE: RNA
<213> ORGANISM: Homo sapiens

<400> SEQUENCE: 5
agcuacaucu ggcuacuggg ucuc                                             24

<210> SEQ ID NO 6
<211> LENGTH: 23
<212> TYPE: RNA
<213> ORGANISM: Homo sapiens

<400> SEQUENCE: 6
agcuacauug ucugcugggu uuc                                              23

<210> SEQ ID NO 7
<211> LENGTH: 21
<212> TYPE: RNA
<213> ORGANISM: Homo sapiens

<400> SEQUENCE: 7
ugugacuggu ugaccagagg g                                                21

<210> SEQ ID NO 8
<211> LENGTH: 23
<212> TYPE: RNA
<213> ORGANISM: Homo sapiens

```
<400> SEQUENCE: 8
cgaauguugc ucggugaacc ccu                                         23

<210> SEQ ID NO 9
<211> LENGTH: 22
<212> TYPE: RNA
<213> ORGANISM: Homo sapiens

<400> SEQUENCE: 9
aacauucauu gcugucggug gg                                          22

<210> SEQ ID NO 10
<211> LENGTH: 18
<212> TYPE: RNA
<213> ORGANISM: Homo sapiens

<400> SEQUENCE: 10
ucuacagugc acgugucu                                               18

<210> SEQ ID NO 11
<211> LENGTH: 21
<212> TYPE: RNA
<213> ORGANISM: Homo sapiens

<400> SEQUENCE: 11
uaacagucuc cagucacggc c                                           21

<210> SEQ ID NO 12
<211> LENGTH: 22
<212> TYPE: RNA
<213> ORGANISM: Homo sapiens

<400> SEQUENCE: 12
ugguuuaccg ucccacauac au                                          22

<210> SEQ ID NO 13
<211> LENGTH: 23
<212> TYPE: RNA
<213> ORGANISM: Homo sapiens

<400> SEQUENCE: 13
caccaagugc auuuaguuga aug                                         23

<210> SEQ ID NO 14
<211> LENGTH: 23
<212> TYPE: RNA
<213> ORGANISM: Homo sapiens

<400> SEQUENCE: 14
cuuagccugu agacaugcug cua                                         23

<210> SEQ ID NO 15
<211> LENGTH: 22
<212> TYPE: RNA
<213> ORGANISM: Homo sapiens

<400> SEQUENCE: 15
ggggcaguag agcuuggaca ga                                          22

<210> SEQ ID NO 16
<211> LENGTH: 23
<212> TYPE: RNA
<213> ORGANISM: Homo sapiens
```

```
<400> SEQUENCE: 16
uucuauguuu uguuugagu gua                                           23

<210> SEQ ID NO 17
<211> LENGTH: 22
<212> TYPE: RNA
<213> ORGANISM: Homo sapiens

<400> SEQUENCE: 17
uuugagugua gccugacugu uu                                           22

<210> SEQ ID NO 18
<211> LENGTH: 24
<212> TYPE: RNA
<213> ORGANISM: Homo sapiens

<400> SEQUENCE: 18 acugggaga cagaaacugu gguu                                          24

<210> SEQ ID NO 19
<211> LENGTH: 23
<212> TYPE: RNA
<213> ORGANISM: Homo sapiens

<400> SEQUENCE: 19
cuggggagac agaaacugug guu                                          23

<210> SEQ ID NO 20
<211> LENGTH: 21
<212> TYPE: RNA
<213> ORGANISM: Homo sapiens

<400> SEQUENCE: 20
cugugguuga uagccaguca c                                            21

<210> SEQ ID NO 21
<211> LENGTH: 23
<212> TYPE: RNA
<213> ORGANISM: Homo sapiens

<400> SEQUENCE: 21
ugguugauag ccagucacug ccu                                          23

<210> SEQ ID NO 22
<211> LENGTH: 23
<212> TYPE: RNA
<213> ORGANISM: Homo sapiens

<400> SEQUENCE: 22
agucacugcc uuaagaacau uug                                          23

<210> SEQ ID NO 23
<211> LENGTH: 23
<212> TYPE: RNA
<213> ORGANISM: Homo sapiens

<400> SEQUENCE: 23
agugagcaau ggaguggcug cca                                          23

<210> SEQ ID NO 24
<211> LENGTH: 23
<212> TYPE: RNA
<213> ORGANISM: Homo sapiens
```

-continued

```
<400> SEQUENCE: 24
aaaaccugga uucccaccug ccg                                              23

<210> SEQ ID NO 25
<211> LENGTH: 23
<212> TYPE: RNA
<213> ORGANISM: Homo sapiens

<400> SEQUENCE: 25
ggaaaccgcc uaguuuacug uuu                                              23

<210> SEQ ID NO 26
<211> LENGTH: 23
<212> TYPE: RNA
<213> ORGANISM: Homo sapiens

<400> SEQUENCE: 26
auguaaucuc ucugcagcug ccg                                              23

<210> SEQ ID NO 27
<211> LENGTH: 23
<212> TYPE: RNA
<213> ORGANISM: Homo sapiens

<400> SEQUENCE: 27
guacuuucug ccacacacug ccu                                              23

<210> SEQ ID NO 28
<211> LENGTH: 23
<212> TYPE: RNA
<213> ORGANISM: Homo sapiens

<400> SEQUENCE: 28
acacagauug cuauaaacug uua                                              23

<210> SEQ ID NO 29
<211> LENGTH: 23
<212> TYPE: RNA
<213> ORGANISM: Homo sapiens

<400> SEQUENCE: 29
acaacauuga uuagguguug uca                                              23

<210> SEQ ID NO 30
<211> LENGTH: 23
<212> TYPE: RNA
<213> ORGANISM: Homo sapiens

<400> SEQUENCE: 30
ccaguacaag aaugucccug cua                                              23

<210> SEQ ID NO 31
<211> LENGTH: 23
<212> TYPE: RNA
<213> ORGANISM: Homo sapiens

<400> SEQUENCE: 31
gagcaucugc ugaaauacug uua                                              23

<210> SEQ ID NO 32
<211> LENGTH: 23
<212> TYPE: RNA
<213> ORGANISM: Homo sapiens
```

-continued

```
<400> SEQUENCE: 32
guauuagugu uucugcauug cca                                          23

<210> SEQ ID NO 33
<211> LENGTH: 19
<212> TYPE: RNA
<213> ORGANISM: Homo sapiens

<400> SEQUENCE: 33
gcuuccagaa gaacaguca                                               19

<210> SEQ ID NO 34
<211> LENGTH: 19
<212> TYPE: RNA
<213> ORGANISM: Homo sapiens

<400> SEQUENCE: 34
ugacuguucu ucuggaagc                                               19

<210> SEQ ID NO 35
<211> LENGTH: 19
<212> TYPE: RNA
<213> ORGANISM: Homo sapiens

<400> SEQUENCE: 35
acgaucaagg aucugaugc                                               19

<210> SEQ ID NO 36
<211> LENGTH: 19
<212> TYPE: RNA
<213> ORGANISM: Homo sapiens

<400> SEQUENCE: 36
gcaucagauc cuugaucgu                                               19

<210> SEQ ID NO 37
<211> LENGTH: 19
<212> TYPE: RNA
<213> ORGANISM: Homo sapiens

<400> SEQUENCE: 37
caugucgauc aagacuuga                                               19

<210> SEQ ID NO 38
<211> LENGTH: 19
<212> TYPE: RNA
<213> ORGANISM: Homo sapiens

<400> SEQUENCE: 38
ucaagucuug aucgacaug                                               19

<210> SEQ ID NO 39
<211> LENGTH: 23
<212> TYPE: DNA
<213> ORGANISM: Artificial Sequence
<220> FEATURE:
<223> OTHER INFORMATION: Synthetic

<400> SEQUENCE: 39
catgagaagt atgacaacag cct                                          23

<210> SEQ ID NO 40
<211> LENGTH: 22
<212> TYPE: DNA
```

```
<213> ORGANISM: Artificial Sequence
<220> FEATURE:
<223> OTHER INFORMATION: Synthetic

<400> SEQUENCE: 40
agtccttcca cgataccaaa gt                                              22

<210> SEQ ID NO 41
<211> LENGTH: 21
<212> TYPE: DNA
<213> ORGANISM: Artificial Sequence
<220> FEATURE:
<223> OTHER INFORMATION: Synthetic

<400> SEQUENCE: 41
aaggggacag tctgaatacc c                                               21

<210> SEQ ID NO 42
<211> LENGTH: 21
<212> TYPE: DNA
<213> ORGANISM: Artificial Sequence
<220> FEATURE:
<223> OTHER INFORMATION: Synthetic

<400> SEQUENCE: 42
aggttcccag gtactgctac a                                               21

<210> SEQ ID NO 43
<211> LENGTH: 22
<212> TYPE: DNA
<213> ORGANISM: Artificial Sequence
<220> FEATURE:
<223> OTHER INFORMATION: Synthetic

<400> SEQUENCE: 43
gatctgatgc gccagtttct aa                                              22

<210> SEQ ID NO 44
<211> LENGTH: 21
<212> TYPE: DNA
<213> ORGANISM: Artificial Sequence
<220> FEATURE:
<223> OTHER INFORMATION: Synthetic

<400> SEQUENCE: 44
actgttccac cacttgtcac c                                               21

<210> SEQ ID NO 45
<211> LENGTH: 22
<212> TYPE: DNA
<213> ORGANISM: Artificial Sequence
<220> FEATURE:
<223> OTHER INFORMATION: Synthetic

<400> SEQUENCE: 45
cagatggctc taacctcagt gg                                              22

<210> SEQ ID NO 46
<211> LENGTH: 23
<212> TYPE: DNA
<213> ORGANISM: Artificial Sequence
<220> FEATURE:
<223> OTHER INFORMATION: Synthetic

<400> SEQUENCE: 46
cacgaaaaag aggctttcta cga                                             23
```